United States Patent
Av-Gay et al.

(10) Patent No.: US 10,039,781 B2
(45) Date of Patent: Aug. 7, 2018

(54) PULSE INHALATION OF NITRIC OXIDE FOR TREATING RESPIRATORY DISEASES

(71) Applicant: Advanced Inhalation Therapies (AIT) Ltd., Beer-Yaacov (IL)

(72) Inventors: Yossef Av-Gay, Vancouver (CA); David Greenberg, Omer (IL); Einav Levi, Beit-SheAn (IL)

(73) Assignee: AIT THERAPEUTICS, INC., Harrison, NY (US)

( * ) Notice: Subject to any disclaimer, the term of this patent is extended or adjusted under 35 U.S.C. 154(b) by 0 days.

(21) Appl. No.: 15/079,328

(22) Filed: Mar. 24, 2016

(65) Prior Publication Data

US 2016/0279165 A1    Sep. 29, 2016

Related U.S. Application Data

(60) Provisional application No. 62/137,341, filed on Mar. 24, 2015.

(51) Int. Cl.
*A61M 16/00* (2006.01)
*A61K 33/00* (2006.01)

(52) U.S. Cl.
CPC ................... *A61K 33/00* (2013.01)

(58) Field of Classification Search
CPC ...... A61M 16/00; A61M 16/10; A61B 5/1455
See application file for complete search history.

(56) References Cited

U.S. PATENT DOCUMENTS

| | | | |
|---|---|---|---|
| 8,518,457 B2* | 8/2013 | Miller | A61K 9/007 128/200.24 |
| 2007/0144515 A1* | 6/2007 | Stenzler | A61M 16/0051 128/203.25 |
| 2012/0107423 A1* | 5/2012 | Goldstein | A61K 33/00 424/718 |

* cited by examiner

*Primary Examiner* — Gina C Justice
(74) *Attorney, Agent, or Firm* — Elmore Patent Law Group, P.C.; Joseph C. Zucchero; Carolyn S. Elmore

(57) ABSTRACT

A method of treating a human subject which is effected by intermittent breathing cycle-coordinated pulse delivery inhalation of gaseous nitric oxide at a concentration of at least 160 ppm, or at a load per cycle of 80 ppm-hour, is disclosed. The method can be utilized for treating a human subject suffering from, or prone to suffer from, a disease or disorder that is manifested in the respiratory tract, or from a disease or disorder that can be treated via the respiratory tract. The disclosed method can be effected while monitoring one or more of on-site and off-site parameters such as vital signs, methemoglobin levels, pulmonary function parameters, blood chemistry and hematological parameters, blood coagulation parameters, inflammatory marker levels, liver and kidney function parameters and vascular endothelial activation parameters, such that no substantial deviation from a baseline in seen in one or more of the monitored parameters.

33 Claims, 4 Drawing Sheets

PULSE INHALATION OF NITRIC OXIDE FOR TREATING RESPIRATORY DISEASES

CROSS REFERENCE TO RELATED APPLICATIONS

Figure 1:
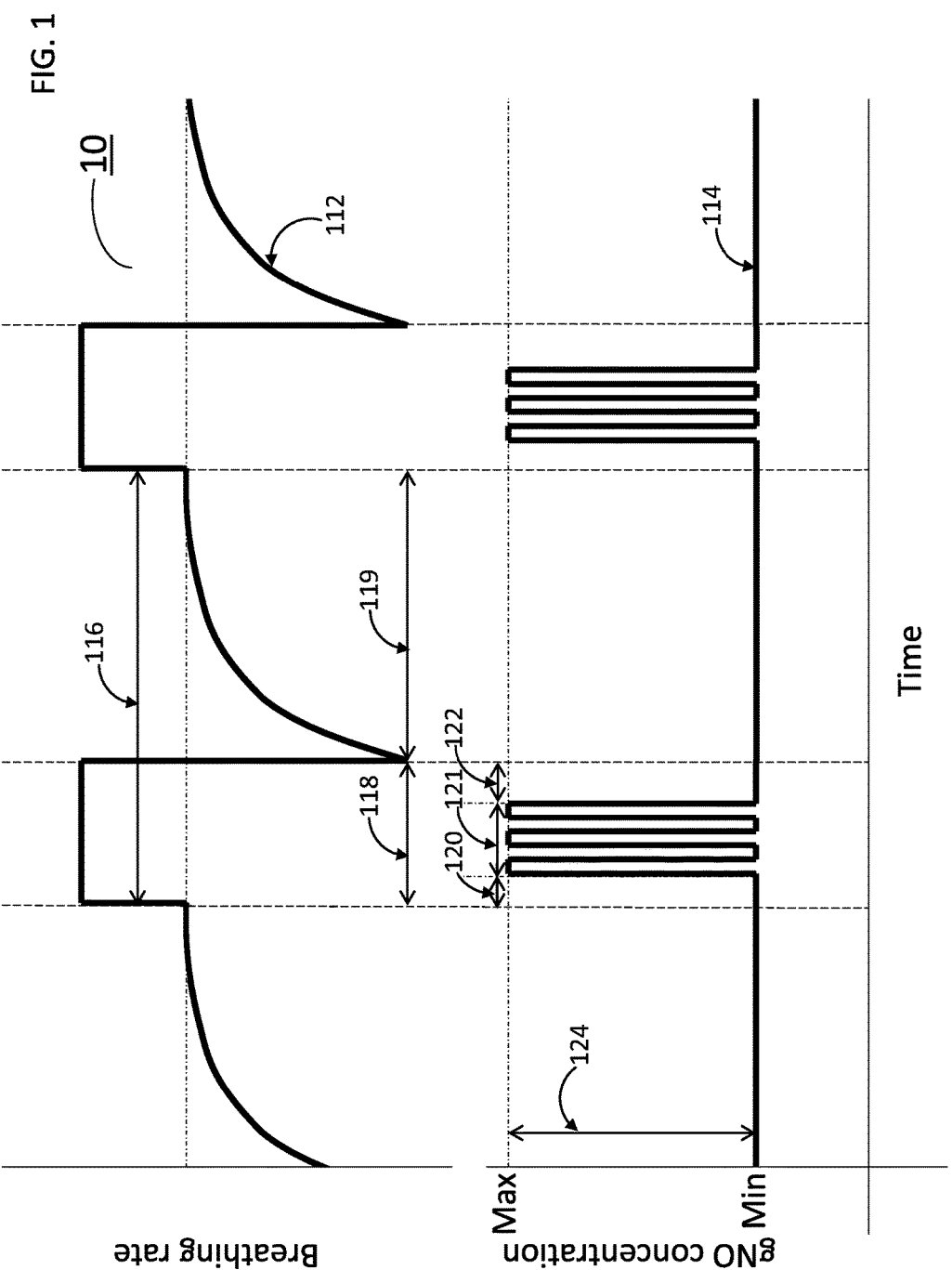

This application claims priority of U.S. Provisional Patent Application Ser. No. 62/137,341, filed on Mar. 24, 2015, the contents of which are hereby incorporated by reference in their entirety.

FIELD AND BACKGROUND OF THE INVENTION

The present invention, in some embodiments thereof, relates to therapy, and more particularly, but not exclusively, to methods and devices for treating respiratory diseases by pulse inhalation of gaseous nitric oxide at concentration of at least 160 ppm or at equivalent load of gaseous nitric oxide.

Nitric oxide (NO) is a small lipophilic signaling molecule with a small stokes radius and a molecular weight of 30 grams/mol that enables it to cross the glycolipid cell plasma membrane into the cytosol readily and rapidly. NO has an unpaired electron available in its outer orbit that characterizes it as a free radical. NO has been shown to play a critical role in various bodily functions, including the vasodilatation of smooth muscle, neurotransmission, regulation of wound healing and immune responses to infections such as caused by bactericidal action directed toward various organisms. NO has been demonstrated to play an important role in wound healing through vasodilatation, angiogenesis, anti-inflammatory and antimicrobial action.

NO is a common air pollutant and is present in concentrations of 150-650 ppm in cigarette smoke and up to 1200 ppm in cigar and pipe smoke. The National Institute for Occupational Safety and Health (OSHA) and the Environmental Protection Agency have given an inhalation threshold limit value (TLV) as a time-weighted average (TWA) of 25 ppm for NO. The TLV-TWA is the concentration to which a person's respiratory system may be exposed continuously throughout a normal work week without adverse effects and, when represented in ppm hours units, is calculated to be 200 ppm hours. This level is a time-weighted average, that is, the average level of NO should be less than 25 ppm; however, brief exposures to higher concentrations are allowed.

NO is produced by the innate immune response in organs and cells exposed to bacterial and viral infections. These include, among others, the nasopharyngeal airway, lungs and circulating neutrophils and macrophages. NO is also a highly reactive microbicidal free radical that possesses antimicrobial activity against broad range of bacteria, parasites, fungi and viruses. The pore diameter in the cell walls of the microorganisms through which the NO molecule must pass to affect these pathogens is approximately five times wider so that there are few barriers to NO cell penetration. NO is therefore an essential part of the innate immune response. In addition, NO is one of the smallest, yet one of the most important, biological signaling molecules in mammals.

Other than being a well-established direct antimicrobial agent, it has been hypothesized that the antimicrobial and cellular messenger regulatory properties of NO, delivered in an exogenous gaseous form, might easily enter the pulmonary milieu and be useful in optimizing the treatment of uncontrolled pulmonary disease with specific actions directed at reducing bacterial burden, reducing inflammation and improving clinical symptoms.

Some respiratory disorders and physiological conditions can be treated by inhalation of gaseous nitric oxide (gNO). The use of gNO by inhalation can prevent, reverse, or limit the progression of disorders such as acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery, acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Inhaled gNO can also be used to treat cystic fibrosis (CF), chronic pulmonary hypertension, bronchopulmonary dysplasia, chronic pulmonary thromboembolism and idiopathic or primary pulmonary hypertension or chronic hypoxia.

From the toxicological aspect, NO has a half-life in the body of less than 6 seconds and a radius of action of approximately 200 microns from its site of origin, beyond which it is inactivated through binding to sulfhydryl groups of cellular thiols or by nitrosylation of the heme moieties of hemoglobin to form methemoglobin (MetHb). MetHb reductase reduces NO to nitrates in the blood serum. Nitrate has been identified as the predominant nitric oxide metabolite excreted in the urine, accounting for more than 70% of the nitric oxide dose inhaled. Nitrate is cleared from the plasma by the kidney at rates approaching the rate of glomerular filtration. Blood levels of MetHb in healthy humans are typically less than 2%.

Potential side effects of high dose NO treatment hence include the binding of NO to hemoglobin and the formation of MetHb, which could lead to decreased oxygen transport, and the capacity of NO to act as a nitrosylating agent on proteins and other cell constituents. Formation of MetHb and increased levels thereof have been observed in previous studies of gNO inhalation by healthy human individuals, wherein inhalation of gNO at 128 ppm for 3 hours and at 512 ppm for 55 minutes has been reported to drive the levels of MetHb over the safe threshold of 5% [Borgese N. et al., *J. Clin. Invest.*, 1987, 80, 1296-1302; Young J. D. et al., *Intensive Care Med.*, 1994, 20, 581-4 and Young J. D. et al., *Brit. J. Anaesthesia*, 1996, 76, 652-656].

Thus, concerns have been raised regarding the potential use of NO as a therapeutic agent in various clinical scenarios. To date, studies indicate that acute pulmonary injury, pulmonary edema, hemorrhage, changes in surface tension of surfactant, reduced alveolar numbers and airway responsiveness may be caused by high airway levels of NO, $NO_2$ and other oxides of nitrogen [Hurford W., *Resp. Care,* 2005, 50, 1428-9].

Several animal studies conducted in order to evaluate the safety window for gNO exposure were reported on the Primary Medical Review of NDA 20-845 (INOmax nitric oxide gas). Included in these reports is the study referred to as RDR-0087-DS, wherein groups of 10 rats each were exposed to room air or to 80, 200, 300, 400 or 500 ppm gNO for 6 continuous hours per day for up to 7 days. It is reported that all of the animals died on the first day of exposure to 400 and 500 ppm gNO with MetHb levels of 72.5 and 67 percents respectively. Six of the animals treated with 300 ppm gNO died during the first 1-2 days. All deaths were attributed to methemoglobinemia.

In additional studies, rats were exposed continuously to room air, 40, 80, 160, 200 and 250 ppm gNO for 6 hours/day for 28 days. No deaths occurred at gNO concentrations below 200 ppm.

At present, inhalation of gaseous nitric oxide (gNO) as a selective, short acting vasodilator is approved only at 80 ppm for use in full term infants with hypoxic respiratory failure associated with pulmonary hypertension. However, other studies have shown that at such low concentration of inhaled gNO, treatment of adults' respiratory diseases is limited, and the use of higher doses of gNO for treating various medical conditions by inhalation requires in-depth safety studies in humans.

Miller et. al. reported the effect of 1,600 ppm hours gNO against five planktonic (suspended in a liquid) species of methicillin resistant *S. aureus* (MRSA). An in vitro biofilm MRSA model was also used to compare gNO to the antibiotic vancomycin as an antibacterial agent. For the biofilm experiment, a drip flow reactor was used to grow a MRSA biofilm which was then exposed for eight hours to Ringers lactate, 200 ppm gNO (1,600 ppm hours), air or vancomycin (100-times MIC level). A reduction in the population of all five MRSA planktonic strains was observed after exposure to 1,600 ppm hours of gNO. In the biofilm experiment gNO was also shown to reduce MRSA.

Additional animal studies have shown that gNO at 160-200 ppm can exert potent antimicrobial effects against a broad range of microbes in vitro, ex vivo and in animal models [Kelly T. J. et al., *J. Clin. Invest.*, 1998, 102, 1200-7; McMullin B. et al., *Resp. Care.*, 2005, 50, 1451-6; Ghaffari A. et al., *Nitric Oxide*, 2005, 12, 129-40; Ghaffari A. et al., *Wound Repair Regen.*, 2007, 15, 368-77; Miller C. C. et al., *J. Cutan. Med. Surg.* 2004, 8, 233-8; Miller C. C. et al., *Nitric Oxide*, 2009, 20, 16-23], further suggesting its use as an antimicrobial agent in appropriate concentrations.

Studies conducted in a rat model of *Pseudomonas aeruginosa* pneumonia tested the antimicrobial effect of a gNO inhaled delivery regimen of intermittent 30 minute exposures of 160-200 ppm gNO, and revealed that 160 ppm gNO in that regiment is effective to reduce the pulmonary bioburden and leukocyte infiltration [Hergott C. A. et al., *Am. J. Resp. Crit. Care Med.*, 2006, 173, A135]. This treatment was also shown to decrease the clinical symptoms of bovine respiratory disease in cattle [Schaefer A. L. et al., *Online J. Vet. Res.*, 2006, 10, 7-16].

Miller, C. C. et al. [*J. Cutan. Med. Surg.*, 2004, 8(4), 233-8] reported on topical treatment of a subject who had a chronic, non-healing wound and presence of a reoccurring biofilm with gNO at a treatment concentration of 200 ppm for two weeks. Within the first three days of treatment, the subject's biofilm was no longer visibly present and at one week, the wound size was reduced by 42%. The subject's ulcer continued to heal following the cessation of nitric oxide exposure.

WO 2005/110441 teaches a method and a corresponding device for combating microbes and infections by delivering intermittent doses of 160-400 ppm gNO to a mammal for a period of time which cycles between high and low concentration of nitric oxide gas. The regimen involves delivery of 160 ppm gNO for 30 minutes every four hours with 0-20 ppm delivered for the 3.5 hours between the higher concentration deliveries. No experimental data are presented in this publication.

U.S. Pat. No. 7,122,018 teaches topical intermittent exposure to concentration of nitric oxide ranging 160-400 ppm, for treatment of infected wounds and respiratory infections by a regimen of 4-hour sessions interrupted by 1 hour of rest while monitored methemoglobin blood levels.

U.S. Pat. No. 7,520,866 teaches topical exposure of wounds to gNO at a high concentration ranging 160-400 ppm with a regime of two 4-hour sessions, interrupted by 1 hour of rest, wherein after a first treatment period with high concentration of gNO, a second treatment period at a lower concentration of 5-20 ppm may be provided to restore the balance of nitric oxide and induce collagen expression to aid in the closure of the wound.

WO 2013/132503 discloses methods and systems for intermittent delivery of gNO, at a concentration of about 160 ppm, by inhalation, to human subjects, while showing that such an administration do not cause substantial change in various parameters of the subject.

Pulsed delivery of inhaled nitric oxide has been developed, as a mean to, for example, reduce the exposure to, and inhalation of, nitrogen dioxide by patients treated for pulmonary arterial hypertension (PAH) and chronic obstructive pulmonary disease (COPD) by gNO inhalation at concentrations lower than 150 ppm [Channick, R. N., et al., *Chest*, 1996, 109(6), p. 1545-9; Nyman, G., et al., *Vet Anaesth Analg*, 2012, 39(5), p. 480-7; Martin A. R. et al., *Medical Gas Research*, 2014, 4(1)]. Clinical studies conducted over the years [Kitamukai O. et al., *Intern Med*, 2002, 41(6), p. 429-34; Barst R. J. et al., *Pulm Circ*, 2012, 2(2), p. 139-47; and 6. Ivy D. D. et al., *J Pediatr*, 199, 133(3), p. 453-6] determined that pulsed delivery of inhaled NO may minimize NO and nitrogen dioxide expiratory concentrations, may utilize lower concentration of NO, may eliminate the need for scavenging device, and may reduce environmental pollution [Heinonen, E. et al., Int Care Med, 2000, 26, p. 1116-23; Heinonen, E. et al., *Vet Anaesth Analg*, 2001, 28, p. 3-11; Heinonen, E. et al., *British Journal of Anaesthesia*, 2002, 88, p. 394-8; Heinonen, E. et al., *British Journal of Anaesthesia*, 2003, 90(3), p. 338-42].

Various NO inhalation devices and components thereof are presented in, for example, U.S. Pat. Nos. 5,558,083, 5,558,083, 5,558,083, 5,732,693, 5,752,504, 6,125,846, 7,114,510, 8,282,966, 8,291,904, 8,291,904, 8,293,284, 8,431,163, 8,573,209 and 8,573,210; while NO inhalation devices configured for pulse delivery of NO for treatment of pulmonary arterial hypertension (PAH) and chronic obstructive pulmonary disease (COPD) are currently under development by commercial firms and presented in, for example, U.S. Pat. Nos. 6,164,276 and 6,109,260.

Additional background art includes U.S. Pat. Nos. 8,518,457, 8,083,997, 8,079,998, 8,066,904, 8,057,742, 7,531,133, 7,516,742, 6,432,077, 7,516,742 and 7,955,294; U.S. Patent Application Nos. 2011/0262335, 2011/0259325, 2011/0240019, 2011/0220103 and 2010/0331405, 2011/0112468, 2008/0287861, 2008/0193566, 2007/0116785, 2007/0104653, 2007/0088316, 2007/0086954, 2007/0065473, 2007/0014688, 2006/0207594, 2005/0191372 and WO 1995/10315, WO 2008/095312, WO 2006/071957, WO 2006/110923, WO 2006/110923, WO 2007/057763, WO 2007/057763, WO 2000/30659 and EP 0692984; Miller C. C. et al., *Antimicrobial Agents And Chemotherapy*, 2007, 51(9), 3364-3366; and Miller C. C. et al., [*Resp Care*, 2008, 53(11), 1530].

SUMMARY OF THE INVENTION

The present invention, in some embodiments thereof, relates to a methodology that utilizes intermittent cycle-coordinated pulse delivery inhalation of gaseous nitric oxide to human subjects at a protocol that results in efficient therapeutic effect while not causing substantial changes in various physiological parameters of the human subject.

Some embodiments of the present invention relate to a methodology that utilizes intermittent cycle-coordinated pulse delivery inhalation of gaseous nitric oxide at a concentration of 160 ppm or more, or at an equivalent load in terms of ppm-hour, to human subjects at a protocol that results in efficient therapeutic effect while not causing substantial changes in various physiological parameters of the human subject.

Exemplary such parameters are those obtainable on-site in real-time, such as methemoglobin level, end-tidal $CO_2$ level, and oxygenation, and parameters which are obtainable off-site in the laboratory, such as blood nitrite level, urine nitrite level, and inflammatory markers' level. Embodiments of the present invention therefore relate to methods of administering gaseous nitric oxide to human subjects in need thereof, in a pulse delivery inhalation, as described herein, such that the above-described parameters remain substantially unchanged. The disclosed administration can be used in methods of treating and/or preventing various medical conditions, which are manifested in the respiratory tract, or which can be treated via the respiratory tract, by subjecting a human subject to intermittent breathing cycle-coordinated pulse delivery inhalation of gaseous nitric oxide at a concentration of 160 ppm or more.

According to an aspect of some embodiments of the present invention, there is provided a method of treating a human subject in need of inhalation of gaseous NO (gNO), the method comprising subjecting the human subject to intermittent inhalation of an inhalant, whereas the intermittent inhalation comprises at least one cycle of a breathing cycle-coordinated pulse delivery inhalation of the inhalant for a first time period, followed by inhalation of essentially no gNO for a second time period, wherein:

the inhalation period of the breathing cycle comprises a pulse delay period, a pulse delivery period and a pulse cessation period;

the inhalant comprises gNO at a concentration of at least 160 ppm during the pulse delivery period; and the inhalant is essentially devoid of gNO during the pulse delay period, the pulse cessation period and the exhalation period of the breathing cycle.

According to another aspect of some embodiments of the present invention, there is provided a method of treating a human subject in need of inhalation of gaseous NO (gNO), which includes subjecting the human subject to intermittent inhalation of an inhalant, whereas the intermittent inhalation includes at least one cycle of a breathing cycle-coordinated pulse delivery inhalation of the inhalant for a first time period, followed by inhalation of essentially no gNO for a second time period, and wherein:

the inhalation period of the breathing cycle includes a pulse delay period, a pulse delivery period and a pulse cessation period;

the inhalant comprises gNO during the pulse delivery period;

the inhalant is essentially devoid of gNO during the pulse delay period, the pulse cessation period and an exhalation period of the breathing cycle; and the breathing cycle-coordinated pulse delivery inhalation is configured to deliver about 80 ppm-hour of gNO in at least one cycle.

According to some embodiments, the concentration of gNO in the inhalant during the pulse delivery period is at least 160 ppm.

According to some embodiments of the present invention, the pulse delay period ranges from 0 ms to 2500 ms.

According to some embodiments, the pulse cessation period ranges from 0 ms to 2500 ms.

According to some embodiments, the pulse delay period comprises at least one pulse-on period followed by a pulse-off period.

According to some embodiments, each of the pulse-on periods individually ranges from 100 ms to 5000 ms.

According to some embodiments, each of the pulse-off period individually ranges from 0 ms to 2500 ms.

According to some embodiments, the pulse-on period is 260 ms.

According to some of any of the embodiments described herein, the first time period is about 30 minutes.

According to some of any of the embodiments described herein, the second time period ranges from 3 to 5 hours.

According to some of any of the embodiments described herein, the inhalation comprises from 1 to 6 of the cycles per day.

According to some of any of the embodiments described herein, the treatment is effected by administering five of the cycles per day.

According to some of any of the embodiments described herein, the intermittent breathing cycle-coordinated pulse delivery inhalation of gNO is effected during a time period that ranges from 1 day to 7 days.

According to some embodiments, during the first time period, the concentration of gNO in the mixture deviates from the predetermined concentration by 10%, or preferably less, e.g. 80 ppm±8 ppm, 160 ppm±16 ppm, 200 ppm±20 ppm and so on.

According to some embodiments, during the first time period, a concentration of $NO_2$ in the mixture is less than 5 ppm.

According to some embodiments, during the first time period, a concentration of $O_2$ in the mixture ranges from 20% to 25%.

According to some embodiments of the present invention, during the first time period, a fraction of inspired oxygen level ($FiO_2$) in the mixture ranges from 21% to 100%.

According to some of any of the embodiments described herein, the method is effected while, or further comprises, monitoring in the subject at least one on-site parameter selected from the group consisting of:

a methemoglobin level (SpMet);

an oxygen saturation level ($SpO_2$); and an end tidal $CO_2$ level ($ETCO_2$), and/or at least one off-site parameter selected from the group consisting of: a serum nitrite/nitrate level ($NO_2^-$/$NO_3^-$); and an inflammatory cytokine plasma level.

According to some embodiments of the present invention, the cytokine is selected from the group consisting of (TNF) α, (IL)-1β, IL-6, IL-8, IL-10 and IL-12p70.

According to some embodiments of the present invention, the monitoring is of at least two of the above-mentioned parameters.

According to some embodiments of the present invention, the monitoring is of all of the above-mentioned parameters.

According to some embodiments of the present invention, a change in the at least one of the above-mentioned monitored parameter following the subjecting is less than 2 acceptable deviation units from a baseline.

According to some embodiments of the present invention, a change in at least one of the above-mentioned monitored parameter following the subjecting is less than 2 acceptable deviation units from a baseline.

According to some embodiments of the present invention, a change in at least two of the above-mentioned monitored parameter following the subjecting is less than 2 acceptable deviation units from a baseline.

According to some embodiments of the present invention, a change in all of the above-mentioned monitored parameters following the subjecting is less than 2 acceptable deviation units from a baseline.

According to some embodiments of the present invention, a change in at least one of, or all of, the above-mentioned on-site parameters following the subjecting is less than 2 acceptable deviation units from a baseline.

According to some embodiments of the present invention, a change in at least one of, or all of, the above-mentioned off-site parameters following the subjecting is less than 2 acceptable deviation units from a baseline.

According to some of any of the embodiments described herein, the method further comprises, or is effected while, monitoring urine nitrite level in the subject.

According to some embodiments of the present invention, a change in the urine nitrite level following the subjecting is less than 2 acceptable deviation units from a baseline.

According to some of any of the embodiments described herein, the method further comprises, or is effected while, monitoring off-site a hematological marker in the subject.

According to some embodiments of the present invention, a change in the hematological parameter following the subjecting is less than 2 acceptable deviation units from a baseline.

According to some of any of the embodiments described herein, the method further comprises, or is effected while, monitoring in the subject at least one off-site parameter selected from the group consisting of:

a vascular endothelial activation factor (e.g., Ang-1, Ang-2 and Ang-2/Ang-1 ratio);

a coagulation parameter (e.g., prothrombin time (PT), a prothrombin ratio (PR) and an international normalized ratio (INR));

a serum creatinine level; and a liver function marker (e.g., an aspartate aminotransferase (AST) level, a serum glutamic oxaloacetic transaminase (SGOT) level, an alkaline phosphatase level, and a gamma-glutamyl transferase (GGT) level).

According to some embodiments of the present invention, a change in at least one, or all of, such parameter(s) following the subjecting is less than 2 acceptable deviation units from a baseline.

According to some of any of the embodiments described herein, the method further comprises, or is effected while, monitoring in the subject at least one on-site parameter selected from the group consisting of:

a vital sign (e.g., a heart rate, a blood pressure, a respiratory rate and a body temperature); and a pulmonary function (e.g., forced expiratory volume ($FEV_1$), maximum mid-expiratory flow (MMEF), diffusing capacity of the lung for carbon monoxide (DLCO), forced vital capacity (FVC), total lung capacity (TLC) and residual volume (RV)).

According to some embodiments of the present invention, no deterioration is observed in at least one, or all of, such parameter(s) during and following the subjecting.

According to some of any of the embodiments described herein, the at least one parameter comprises $ETCO_2$ and during and following the subjecting, the $ETCO_2$ is less than 60 mmHg.

According to some of any of the embodiments described herein, the at least one parameter comprises SpMet and during and following the subjecting, the SpMet is increased by less than 5%.

According to some of any of the embodiments described herein, the at least one parameter comprises $SpO_2$ and during the subjecting, a level of the $SpO_2$ is higher than 89%.

According to some of any of the embodiments described herein, the at least one parameter comprises serum nitrite/nitrate level and during and following the subjecting, a level of the serum nitrite is less than 2.5/25 micromole per liter respectively.

According to some of any of the embodiments described herein, the human subject is suffering from a disease or disorder that is manifested in the respiratory tract or from a disease or disorder that can be treated via the respiratory tract.

According to some of any of the embodiments described herein, the human subject is suffering from a disease or disorder of an otolaryngological and/or an upper respiratory tract and/or a lower respiratory system.

According to some of any of the embodiments described herein, the disease or disorder is selected from the group consisting of a heparin-protamine reaction, a traumatic injury, a traumatic injury to the respiratory tract, acidosis or sepsis, acute mountain sickness, acute pulmonary edema, acute pulmonary hypertension, acute pulmonary thromboembolism, adult respiratory distress syndrome, an acute pulmonary vasoconstriction, aspiration or inhalation injury or poisoning, asthma or to status asthmaticus, bronchopulmonary dysplasia, hypoxia or chronic hypoxia, chronic pulmonary hypertension, chronic pulmonary thromboembolism, cystic fibrosis (CF), fat embolism of the lung, haline membrane disease, idiopathic or primary pulmonary hypertension, inflammation of the lung, perinatal aspiration syndrome, persistent pulmonary hypertension of a newborn, and post cardiac surgery.

According to some of any of the embodiments described herein, the disease or disorder is selected from the group consisting of a bacterial-, viral- and/or fungal bronchiolitis, a bacterial-, viral- and/or fungal pharyngitis and/or laryngotracheitis, a bacterial-, viral- and/or fungal pneumonia, a bacterial-, viral- and/or fungal sinusitis, a bacterial-, viral- and/or fungal upper and/or lower respiratory tract infection, a bacterial-, viral- and/or fungal-exacerbated asthma, a respiratory syncytial viral infection, bronchiectasis, bronchitis, chronic obstructive lung disease (COPD), cystic fibrosis (CF), emphysema, otitis, otitis media, primary ciliary dyskinesia (PCD), aspergilloma, pulmonary aspergillosis (ABPA), and cryptococcosis.

According to some of any of the embodiments described herein, the disease or disorder is associated with a pathogenic microorganism.

According to some of any of the embodiments described herein, the pathogenic microorganism is selected from the group consisting of a Gram-negative bacterium, a Gram-positive bacterium, a virus, a fungus and a parasite.

According to some of any of the embodiments described herein, the disease or disorder is selected from the group consisting of a bacterial-, viral- and/or fungal bronchiolitis, a bacterial-, viral- and/or fungal pharyngitis and/or laryngotracheitis, a bacterial-, viral- and/or fungal sinusitis, a bacterial-, viral- and/or fungal upper and/or lower respiratory tract infection, a bacterial-, viral- and/or fungal-exacerbated asthma, a bacterial-, viral-, fungal- and/or parasitic pneumonia, a common cold, a cystic fibrosis related infection, a respiratory syncytial viral infection, acidosis or sepsis, an oral fungal infection, bronchitis, candidiasis of the oral cavity (thrush), canker sores, epiglottitis (supraglottitis), halitosis, herpes, laryngitis, laryngotracheitis, nasopharyngitis, otitis and otitis media, pharyngitis, aspergilloma, pulmonary aspergillosis (ABPA), cryptococcosis, respiratory syncytial virus infection, a bacterial-, viral- and/or fungal conjunctivitis and uveitis, rhinitis, rhinopharyingitis, rhinosinusitis, stomatitis, tonsillitis, tracheitis, tuberculosis, tympanitis.

According to some of any of the embodiments described herein, the human to subject is suffering from a disease or disorder selected from the group consisting of a bacterial-, viral- and/or fungal bronchiolitis, a bacterial-, viral- and/or fungal pharyngitis and/or laryngotracheitis, a bacterial-, viral- and/or fungal pneumonia, a bacterial-, viral- and/or fungal sinusitis, a bacterial-, viral- and/or fungal upper and/or lower respiratory tract infection, a bacterial-, viral- and/or fungal-exacerbated asthma, a respiratory syncytial viral infection, bronchiectasis, bronchitis, chronic obstructive lung disease (COPD), cystic fibrosis (CF), emphysema, otitis, otitis externa, otitis media, primary ciliary dyskinesia (PCD), aspergilloma, cryptococcosis and pulmonary aspergillosis (ABPA).

According to some of any of the embodiments described herein, the human subject is suffering from bronchiolitis.

According to some of any of the embodiments described herein, the human subject is an immuno-compromised human subject.

According to some embodiments of the present invention, the immune-compromised human subject is selected from the group consisting of a subject suffering from HIV, a subject suffering from cancer, a subject undergoing or which underwent chemotherapy, and a subject undergoing or which underwent transplantation.

According to some of any of the embodiments described herein, the human subject is prone to suffer from a disease or disorder that is manifested in the respiratory tract or from a disease or disorder that can be treated via the respiratory tract.

According to some embodiments of the present invention, the human subject is selected from the group consisting of an immune-compromised subject human a subject suffering from chronic asthma, a subject suffering from chronic sinusitis, a subject exposed to an infectious respiratory tract disease or disorder and a subject exposed to a pathogen.

According to some of any of the embodiments of the invention, the immune-compromised human subject is selected from the group consisting of a subject suffering from HIV, a subject suffering from cancer, a subject undergoing or which underwent chemotherapy, and a subject undergoing or which underwent transplantation.

According to some of any of the embodiments described herein, the human to subject is suffering from a disease or disorder that is manifested in the respiratory tract or a disease or disorder that can be treated via the respiratory tract, the disease or disorder being associated with a nosocomial infection.

According to some of any of the embodiments described herein, the human subject is prone to suffer from, or being at risk of suffering from, a disease or disorder that is manifested in the respiratory tract or a disease or disorder that can be treated via the respiratory tract, the disease or disorder being associated with a nosocomial infection.

According to some embodiments, the human subject is prone to suffer the disease or disorder due to general, environmental and occupational conditions.

According to some embodiments, the human subject is selected from the group consisting of elderly people, medical staff and personnel (doctors, nurses, caretakers and the likes) of medical facilities and other care-giving homes and long-term facilities, commercial airline crew and personnel (pilots, flight attendants and the likes), livestock farmers and the likes.

According to some of any of the embodiments described herein, the nosocomial infection is an infection stemming from direct-contact transmission, indirect-contact transmission, droplet transmission, airborne transmission, common vehicle transmission and vector borne transmission.

According to some of any of the embodiments described herein, the nosocomial infections is caused by an antibiotic resistant bacterium.

According to some embodiments, the bacterium is selected from the group consisting of carbapenem-resistant *Klebsiella* (KPC) or other Enterobacteriaceae, methicillin resistance *Staphylococcus Aureus* (MRSA), Group A *Streptococcus, Staphylococcus aureus* (methicillin sensitive or resistance), *Neisseria meningitides* of any serotype and the likes.

According to some of any of the embodiments described herein, the human subject is suffering from a disease or disorder that is manifested in the respiratory tract or a disease or disorder that can be treated via the respiratory tract, the disease or disorder being an opportunistic infection in an immuno-compromised subject.

According to some of any of the embodiments described herein, the human subject is prone to suffer from, or being at risk of suffering from, a disease or disorder that is manifested in the respiratory tract or a disease or disorder that can be treated via the respiratory tract, the disease or disorder being an opportunistic infection in an immuno-compromised subject.

According to an aspect of some embodiments of the present invention there is provided a method of treating a human subject suffering from bronchiolitis, the method comprising subjecting the subject to intermittent breathing cycle-coordinated pulse delivery inhalation of gNO at a concentration of at least 160 ppm, as described herein, thereby treating the human subject.

According to some of embodiments of the invention, the bronchiolitis is associated with a virus.

According to some of embodiments of the invention, the virus is selected from the group consisting of a respiratory syncytial virus (RSV), a rhinovirus, a coronavirus, an enterovirus, an influenza A and/or B virus, a parainfluenza 1, 2 and/or 3 virus, a bocavirus, a human metapneumovirus, SARS and an adenovirus.

According to an aspect of some embodiments of the invention, there is provided a method of treating a human subject suffering from a medical condition selected form the group consisting of asthma, cystic fibrosis, influenza, and COPD, the method comprising subjecting the subject to intermittent breathing cycle-coordinated pulse delivery inhalation of gNO at a concentration of at least 160 ppm as described herein, thereby treating the human subject.

According to an aspect of some embodiments of the invention, there is provided a method of treating a human subject suffering from a disease or disorder selected from the group consisting of an acute respiratory disease or disorder, a chronic respiratory disease or disorder, an obstructive respiratory disease or disorder, an intrinsic or extrinsic restrictive respiratory disease or disorder, a pulmonary vascular disease or disorder, an infectious respiratory disease or disorder, an inflammatory respiratory disease or disorder, a pleural cavity disease or disorder, and a neonatal respiratory disease or disorder, the method comprising subjecting the subject to intermittent breathing cycle-coordinated pulse delivery inhalation of gNO at a concentration of at least 160 ppm, as described herein, thereby treating the human subject.

According to an aspect of some embodiments of the invention, there is provided a method of treating a human subject suffering from a disease or disorder that is manifested in the respiratory tract or a disease or disorder that can be treated via the respiratory tract, the method comprising subjecting the subject to intermittent breathing cycle-coordinated pulse delivery inhalation of gNO at a concentration of at least 160 ppm, as described herein, thereby treating the disease or disorder.

According to some of embodiments of the invention, the human subject suffers from any of the diseases and disorders described herein.

According to some of embodiments of the invention, the disease or disorder is selected from the group consisting of a bacterial-, viral- and/or fungal bronchiolitis, a bacterial-, viral- and/or fungal pharyngitis and/or laryngotracheitis, a bacterial-, viral- and/or fungal pneumonia, a bacterial-, viral- and/or fungal sinusitis, a bacterial-, viral- and/or fungal upper and/or lower respiratory tract infection, a bacterial-, viral- and/or fungal-exacerbated asthma, a bacterial-, viral- and/or fungal conjunctivitis and uveitis, a respiratory syncytial viral infection, bronchiectasis, bronchitis, chronic obstructive lung disease (COPD), cystic fibrosis (CF), emphysema, otitis, otitis externa, otitis media, primary ciliary dyskinesia (PCD), aspergilloma, cryptococcosis and pulmonary aspergillosis (ABPA).

According to some of embodiments of the invention, the disease or disorder is an ophthalmological, otolaryngological and/or upper respiratory tract disease or disorder.

According to some of embodiments of the invention, the ophthalmological, otolaryngological and/or upper respiratory tract disease and disorder involves an infection or an inflammation of a bodily site selected from the group consisting of an ear cavity, a nasal cavity, an eye, a sinus cavity, an oral cavity, a pharynx, a epiglottis, a vocal cord, a trachea, an apex and an upper esophagus.

According to some of embodiments of the invention, the otolaryngological and/or upper respiratory tract disease and disorder is selected from the group consisting of a common cold, a stomatognathic disease, amigdalitis, an oral fungal infection, bacterial-, viral- and/or fungal sinusitis, bronchitis, candidiasis of the oral cavity (thrush), canker sores, epiglottitis (supraglottitis), halitosis, herpes, laryngitis, laryngotracheitis, nasopharyngitis, otitis, otitis externa, otitis media, conjunctivitis, uveitis, pharyngitis, rhinitis, rhinopharyingitis, rhinosinusitis, stomatitis, tonsillitis, tracheitis, tracheitis and tympanitis.

According to some of embodiments of the invention, the disease or disorder is to a disease or disorder of the lower respiratory system of a human subject.

According to some of embodiments of the invention, the disease or disorder is selected from the group consisting of an obstructive condition, a restrictive condition, a vascular disease and an infection, an inflammation due to inhalation of foreign matter and an inhaled particle poisoning.

According to some of embodiments of the invention, the obstructive condition selected from the group consisting of a chronic obstructive lung disease (COPD), emphysema, bronchiolitis, bronchitis, asthma and viral, bacterial and fungal exacerbated asthma; the restrictive condition selected from the group consisting of fibrosis, cystic fibrosis, sarcoidosis, alveolar damage and pleural effusion; the vascular disease selected from the group consisting of pulmonary edema, pulmonary embolism and pulmonary hypertension; the infection selected from the group consisting of respiratory syncytial virus infection, tuberculosis, viral-, bacterial-, fungal-, and/or parasitic pneumonia, idiopathic pneumonia; and the inflammation due to inhalation of foreign matter and an inhaled particle poisoning selected from the group consisting of smoke inhalation, asbestosis and exposure to particulate pollutants and fumes.

According to some of embodiments of the invention, the human subject is selected from the group consisting of an immune-compromised subject human a subject suffering from chronic asthma, a subject suffering from chronic sinusitis, a subject exposed to an infectious respiratory tract disease or disorder and a subject exposed to a pathogen.

According to some of embodiments of the invention, the immune-compromised human subject is selected from the group consisting of a subject suffering from HIV, a subject suffering from cancer, a subject undergoing or which underwent chemotherapy, and a subject undergoing or which underwent transplantation.

According to an aspect of some embodiments of the present invention there is provided a method of treating a human subject prone to suffer from a disease or disorder that is manifested in the respiratory tract or a disease or disorder that can be treated via the respiratory tract, the method comprising subjecting the subject to intermittent breathing cycle-coordinated pulse delivery inhalation of gNO at a concentration of at least 160 ppm, as described herein, thereby treating or preventing the disease or disorder.

According to some of embodiments of the invention, the human subject is selected from the group consisting of an immune-compromised subject human, a subject suffering from chronic asthma, a subject suffering from chronic sinusitis, a subject exposed to an infectious respiratory tract disease or disorder and a subject exposed to a pathogen.

According to some of embodiments of the invention, the immune-compromised human subject is selected from the group consisting of a subject suffering from HIV, a subject suffering from cancer, a subject undergoing or which underwent chemotherapy, and a subject undergoing or which underwent transplantation.

According to some of any of the embodiments described herein in the context of methods of treating or preventing as described herein, the method further comprises monitoring, during and following the subjecting, at least one parameter selected from the group consisting of:
 a methemoglobin level (SpMet);
 an oxygen saturation level ($SpO_2$);
 an end tidal $CO_2$ level ($ETCO_2$);
 a fraction of inspired oxygen level ($FiO_2$);
 a serum nitrite level ($NO_2^-$); and
 an inflammatory cytokine plasma level,
 in the subject, as described herein.

According to some of embodiments of the invention, a change in the at least one parameter following the subjecting is less than 2 acceptable deviation units from a baseline.

According to some of any of the embodiments described herein in the context of methods of treating or preventing as described herein, the method further comprises monitoring nitrite level in a urine sample of the subject.

According to some of any of the embodiments described herein in the context of methods of treating or preventing as described herein, the method further comprises monitoring at least one parameter selected from the group consisting of:
 a hematological marker;
 a vascular endothelial activation factor;
 a serum creatinine level;
 a liver function marker;

a vital sign;

a pulmonary function; and a coagulation parameter.

According to some of any of the embodiments described herein in the context of methods of treating or preventing as described herein, the subjecting to intermittent breathing cycle-coordinated pulse delivery inhalation of gNO is effected according to any of the embodiments described herein.

According to some embodiments, the subjecting is effected by an inhalation device selected from the group consisting of stationary inhalation device, a portable inhaler, a metered-dose inhaler, an atmospherically controlled enclosure and an intubated inhaler.

According to some embodiments, the subjecting is effected by any of the inhalation devices, systems and methodologies as described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 2:
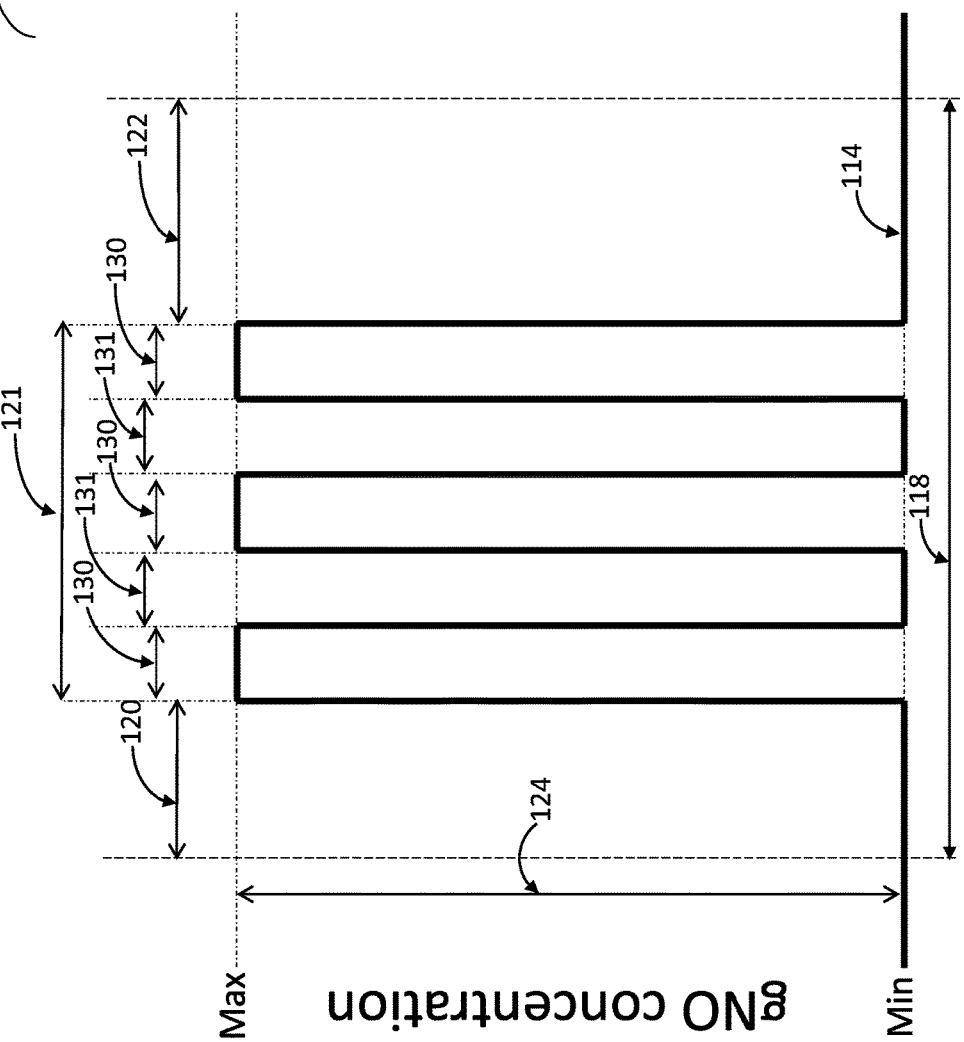
Figure 3:
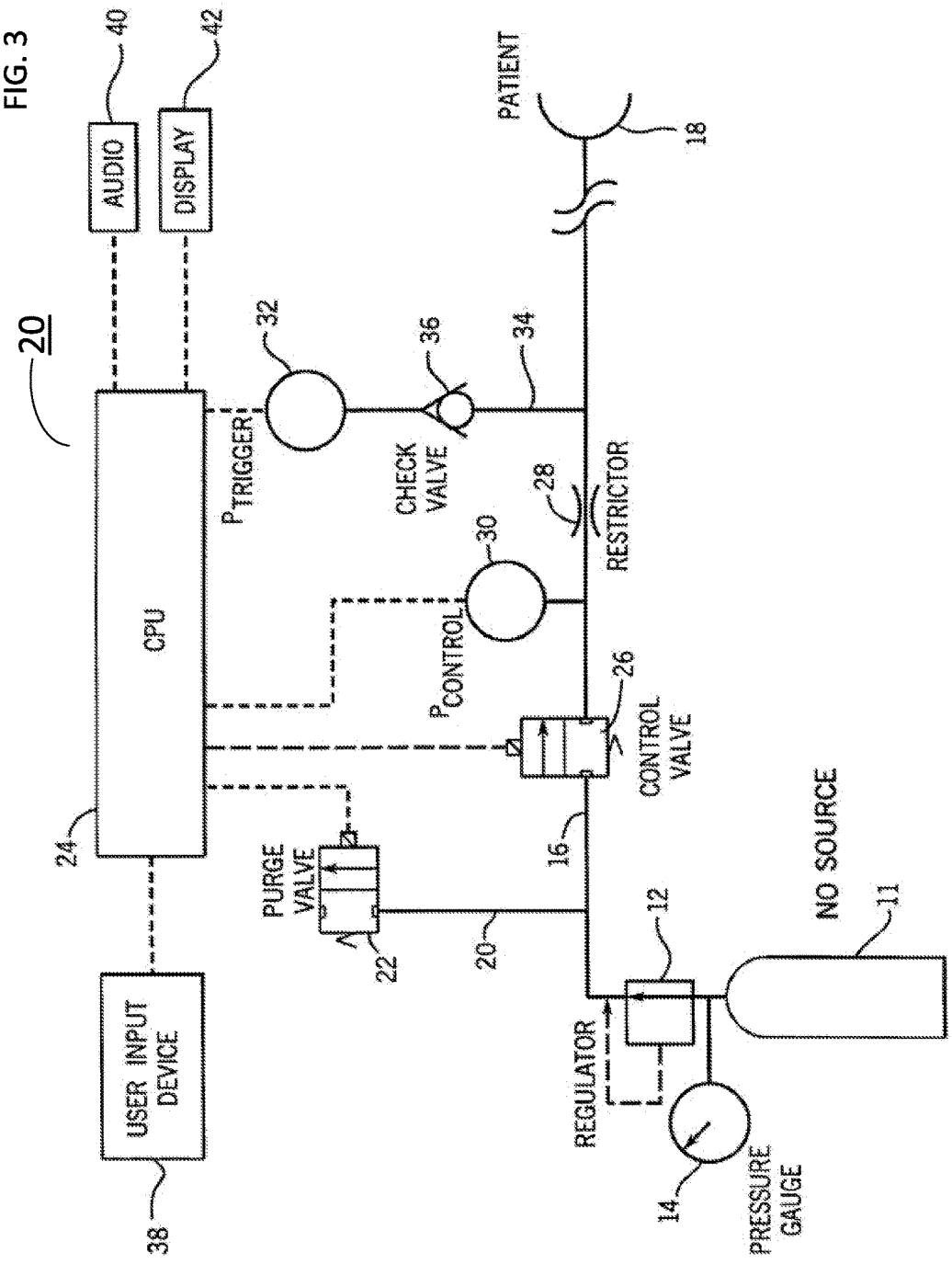
Figure 4:
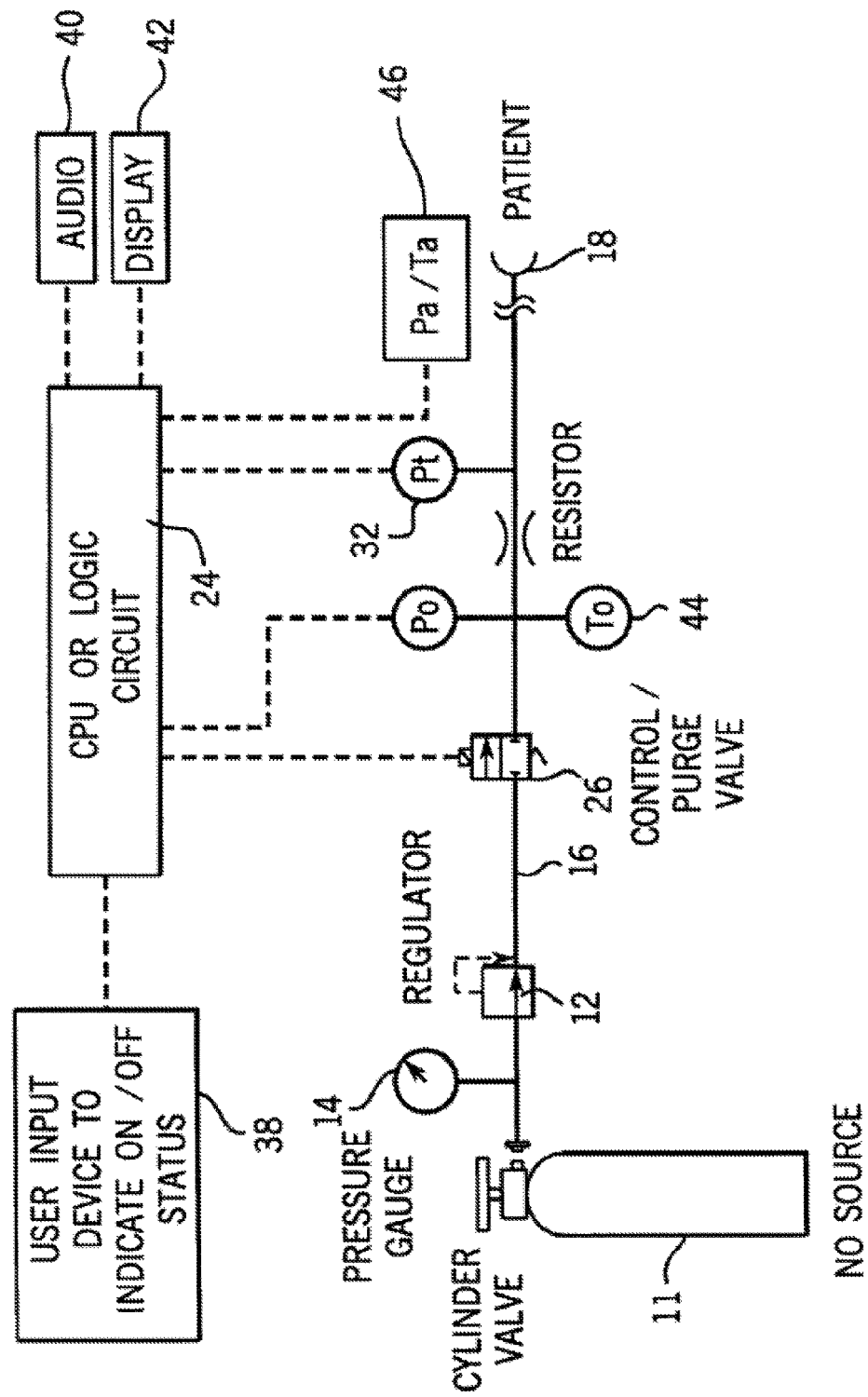

In the drawings:

FIG. 1 presents breathing cycle-coordinated pulse delivery inhalation scheme 10, showing inhalant flow curve 112 and NO concentration curve 114 on a common time scale, wherein breathing cycle period 116 comprises inhalation period 118, during which NO is delivered, and exhalation period 119, during which NO is not used;

FIG. 2 presents a zoom-in view of breathing cycle-coordinated pulse delivery inhalation scheme 10 spanning inhalation period 118, as show in FIG. 1, wherein pulse delivery period 121 comprises three pulses, each spanning pulse-on period 130, interrupted by pulse-off period 131;

FIG. 3 is a schematic illustration of an exemplary breathing cycle-coordinated pulse delivery inhalation device, according to some embodiments of the present invention; and FIG. 4 is a schematic illustration of another exemplary breathing cycle-coordinated pulse delivery inhalation device, according to alternative embodiments of the present invention.

DESCRIPTION OF SPECIFIC EMBODIMENTS OF THE INVENTION

The present invention, in some embodiments thereof, relates to therapy, and more particularly, but not exclusively, to methods and devices for treating respiratory diseases by pulse inhalation of gaseous nitric oxide at concentration of at least 160 ppm or at equivalent load thereof.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, inhalation of gaseous nitric oxide (gNO) has been shown to be a highly effective broad-spectrum antimicrobial therapy.

In vitro studies of the antimicrobial and antiviral effect of gNO have shown that the viability and vitality of viruses, bacteria and fungi decreases to a point of substantial eradication after the pathogen has been exposed to a certain amount of nitric oxide over a certain period of time. This amount, which can be referred to as the effective amount, can be estimated in terms of the concentration of NO in the gas mixture contacted with the pathogen, times the duration of the exposure. For example, the effective amount can be estimated in units of ppm-time-hour, or ppm-hour. Table 1 presents experimental data gathered for microorganisms exposed to 200 ppm gNO until the microorganisms are substantially eradicated*.

However, at effective antimicrobial concentration gNO may present serious adverse effects on humans, hence, the currently approved dose of 80 ppm gNO is presumably too low to exert sufficient antimicrobial effects.

TABLE 1

| Microorganism | Effective amount in ppm-hour |
| --- | --- |
| S. aureus (ATCC) | 800 |
| P. aeruginosa (ATCC) | 600 |
| MRSA | 1000 |
| Serracia sp. | 1200 |
| S. aureus (Clinical) | 800 |
| Klebsiella sp. #1 | 1200 |
| Klebsiella sp.#2 | 1000 |
| Klebsiella sp. #3 | 1200 |
| S. maltophilia | 800 |
| Enterobacter sp. | 1200 |
| Acinetobader sp. | 1200 |
| Candida albicans | 800 |
| Mycobacterium smegmatis | 2000 |
| E. coli | 1000 |
| Group B Streptococci | 400 |
| Average | 1013.33 |
| Standard deviation | 366.19 |

[* adapted from Chris C. Miller, PhD thesis, University of British Columbia, Canada, 2004].

As further discussed hereinabove, intermittent dosing and delivery by inhalation of gNO, cycling between high concentrations of gNO for a relatively short period of time and longer periods of no or low concentration of gNO has been suggested for overcoming the problems of NO toxicity. It has been suggested that the high concentration of gNO, delivered according to an intermittent regimen, would be to effective in overwhelming the nitric oxide defense mechanisms of pathogens.

It has been further suggested in the art that the high concentration of gNO may be delivered at a concentration of between 80 ppm to 300 ppm, and that the time periods for delivering the high concentration should afford a daily delivery of 600 to 2000 ppm hours.

Clinical studies of methods for treating various bacterial, viral and protozoal infections have demonstrated that 30 minutes of inhalation of continuous high concentrations of gNO (e.g., 160 ppm or higher) do not cause lung injury or other signs of adverse effects in humans and even improve some vital effects such as lung function and heart rate. Specifically, prospective phase I open label safety study in healthy adults, who inhaled 160 ppm gNO for 30 minutes, five times a day, for five consecutive days have demonstrated that neither significant adverse events nor adverse events attributable to gNO inhalation occurred and all individuals tolerated the gNO treatment courses well. Forced expiratory volume in 1 sec ($FEV_1$) percentage and other lung function parameters were improved and serum nitrites/nitrates, prothrombin, pro-inflammatory cytokine and chemokine levels, did not differ between baseline and day 5, while methemoglobin levels increased during the study period to a tolerated and accepted level of 0.9%. It was thus demonstrated that inhalation of 160 ppm gNO or more for 30 minutes, about 5 times daily, for 2-7 consecutive days, is safe and well tolerated in healthy individuals.

WO 2013/132503 discloses methods and systems for intermittent delivery of gNO, at a concentration of about 160 ppm, by inhalation, to human subjects, while showing that such an administration do not cause substantial change in various parameters of the subject.

The present invention, in some embodiments thereof, provides methods of treating human subjects by intermittent breathing cycle-coordinated pulse delivery inhalation of high concentration (or load) of gNO, as determined by the concentration of gNO in the inhalant (the mixture of gases which is actually being inhaled by the subject) or the amount of inhaled gNO, which is delivered to the subject in pulses of nitric oxide, according to a scheme referred to herein as breathing cycle-coordinated pulse delivery inhalation. In some embodiments, the methods disclosed herein are to effected while monitoring various parameters relevant for maintaining the desired dosage and regimen, relevant to the safety of the procedure and relevant for efficacy of the treatment.

According to an aspect of some embodiments of the present invention, there is provided a method of treating a human subject in need of inhalation of gaseous NO (gNO), which is effected by subjecting the human subject to intermittent breathing cycle-coordinated pulse delivery inhalation of gNO at a concentration of at least 160 ppm.

According to some embodiments of the invention, subjecting the human subject to gNO intermittent breathing cycle-coordinated pulse delivery inhalation is effected by intermittently subjecting the human subject to a gaseous mixture (the inhalant) by breathing cycle-coordinated pulse delivery, which contains gNO at the indicated concentration (a gNO-containing gaseous mixture).

According to an alternative aspect of some embodiments of the present invention, there is provided a method of treating a human subject in need of inhalation of gaseous NO (gNO); the method includes subjecting the human subject to intermittent inhalation of an inhalant, whereas the intermittent inhalation includes at least one cycle of a breathing cycle-coordinated pulse delivery inhalation of the inhalant for a first time period, followed by inhalation of essentially no gNO for a second time period, wherein the breathing cycle-coordinated pulse delivery inhalation is configured to deliver about 80 ppm-hour of gNO during at least one cycle.

In the context of embodiments of the present invention, the term "load" refers to a certain cumulative amount of nitric oxide to which a subject, or a pathogen, is exposed to during inhalation treatment (e.g., the presently claimed treatment), which is estimated in terms of ppm-hour, namely the average concentration of NO in the inhalant multiplied by the overall time of exposure. The load can be estimated per cycle of the treatment (load per cycle), or per a time unit, such as a day (daily load).

According to some embodiments of the present invention, the intermittent delivery of gNO to the subject is conducted such that the subject inhales gNO at a load that ranges from 600 ppm-hour to 2000 ppm-hour daily, wherein the intermittent delivery is effected such that the daily load is inhaled in more than one session of uninterrupted administration.

According to some embodiments of the present invention, the intermittent to delivery is effected such that the daily load is inhaled in one or more sessions of intermittent breathing cycle-coordinated pulse delivery inhalation, while the load per cycle of each cycle is at least about 80 ppm-hour. Such load per cycle can be obtained, for example, by configuring the pulse(s) to deliver, during one cycle, an inhalant having 160 ppm of NO for 30 minutes (the first time period). It is noted that other concentrations and other first time periods, which afford a load of at least 80 ppm-hour per cycle, are also contemplated and encompassed by embodiments of the present invention. The term "intermittent" is used herein and in the art as an antonym of "continuous", and means starting and ceasing an action and/or performing an action in intervals. The intermittent treatment regimen can be referred to as treatment by sessions, whereas in each session the subject inhales a gNO-containing gaseous mixture for a set period of time, interrupted by a period of time in which the subject inhales gaseous mixture essentially devoid of gNO.

By "intermittent breathing cycle-coordinated pulse delivery inhalation" it is meant that the subject is subjected to a gaseous mixture that contains the indicated concentration of gNO intermittently, and thus inhales such a gNO-containing gaseous mixture by breathing cycle-coordinated pulse delivery two or more times with intervals between each inhalation. The subject therefore inhales the gNO-containing gaseous mixture, then stops inhaling a gNO-containing gaseous mixture by breathing cycle-coordinated pulse delivery and inhales instead a gaseous mixture that does not contain the indicated concentration of gNO (e.g., air), then inhales again the gNO-containing gaseous mixture by breathing cycle-coordinated pulse delivery, and so on and so forth.

In some embodiments of this aspect of the present invention, "a gNO-containing gaseous mixture" is used to describe a gaseous mixture that contains at least 160 ppm gNO. The gNO-containing mixture can comprise 160 ppm, 170 ppm, 180 ppm, 190 ppm, 200 ppm and even higher concentrations of gNO. Other gaseous mixtures mentioned herein include less than 160 ppm gNO or are being essentially devoid of gNO, as defined herein.

In some embodiments "a gNO-containing gaseous mixture" describes a gaseous mixture that delivers gNO at 80 ppm-hour.

By "essentially devoid of gNO" it is meant no more than 50 ppm, no more than 40 ppm, no more than 30 ppm, no more than 20 ppm, no more than 10 ppm, no more than 5 ppm, no more than 1 ppm and no more than ppb, including absolutely no gNO.

According to some embodiments of the present invention, the intermittent breathing cycle-coordinated pulse delivery inhalation includes one or more cycles, each cycle comprising breathing cycle-coordinated pulse delivery inhalation of a gaseous mixture containing gNO at the specified concentration (e.g., at least 160 ppm) for a first time period, which is also referred to herein as the load per cycle, followed by inhalation of a gaseous mixture containing no gNO for a second time period. According to some embodiments of the present invention, during the second period of time the subject may inhale ambient air or a controlled mixture of gases which is essentially devoid of gNO, as defined herein.

In some embodiments, the first time period spans from 10 to 45 minutes, or from 20 to 45 minutes, or from 20 to 40 minutes, and according to some embodiments, spans about 30 minutes.

According to some embodiments of the present invention, the second time period ranges from 3 to 5 hours, or from 3 to 4 hours, and according to some embodiments the second time period spans about 3.5 hours.

According to some embodiments of the present invention, this inhalation regimen is repeated 1-6 times over 24 hours, depending on the duration of the first and second time periods.

In some embodiments, a cycle of intermittent breathing cycle-coordinated pulse delivery of gNO, e.g., 160 ppm for 30 minutes followed by 3.5 hours of breathing no gNO, is repeated from 1 to 6 times a day. According to some embodiments, the cycles are repeated 5 times a day.

In some embodiments, a cycle of intermittent breathing cycle-coordinated pulse delivery of gNO, e.g., at a load of 80 ppm-hour per cycle, followed by 3.5 hours of breathing no gNO, is repeated from 1 to 6 times a day. According to some embodiments, the cycles are repeated 5 times a day.

According to some embodiments of the present invention, the regimen of 1-5 cycles per day is carried out for 1 to 7 days, or from 2 to 7 days, or from 3 to 7 days. According to some embodiments of the present invention, the intermittent breathing to cycle-coordinated pulse delivery inhalation is effected during a time period of 5 days. However, longer time periods of intermittent gNO administration as described herein, are also contemplated.

According to embodiments of the present invention, the gNO-containing gaseous mixture, which the subject inhales during the first time period, is generated in-situ in an inhalation device which is configured to respond to the subject's breathing cycle such that NO is mixed into the inhalant in one or more pulses when the subject breaths in at a high rate, namely at the inhalation period of the breathing cycle. This mode of administration of NO by inhalation is referred to herein as "breathing cycle-coordinated pulse delivery inhalation".

In the context of embodiments of the present invention, the term "pulse" refers to a mode of administering NO, which is introduced into the inhalant in interrupted and concentrated doses during a predetermined period of time, referred to herein as the "pulse delivery period", wherein each pulse, effected during the pulse delivery period, spans a predetermined period of time, referred to herein as the "pulse-on period", and interrupted by a "pulse-off period".

According to embodiments of the present invention, the pulse delivery period starts during the inhalation period, after a period of time which is referred to herein as the "pulse delay period". According to some embodiments of the present invention, the pulse delivery period is typically shorter than the inhalation period, and the time between the end of the pulse delivery period and the end of the inhalation period is referred to herein as the "pulse cessation period".

According to some embodiments of the present invention, the inhalation device for delivering the breathing cycle-coordinated pulse delivery inhalation of gashouse nitric oxide is configured to detect the various phases of the breathing cycle, namely the onset of the inhalation and the exhalation periods, and can therefore coordinate the pulses with the breathing cycle such that the pulse delay period is coordinated to start as soon as the rate of intake increases at the onset of the inhalation period, and the pulse cessation period is coordinated to start with as soon as the rate of intake decreases close to the end of the inhalation period.

In some embodiments, the length of the various time periods in the breathing cycle-coordinated pulse delivery inhalation scheme is determined and/or calculated relative to the duration of the breathing cycle, namely in percents of the total duration to of the breathing cycle, or parts thereof. For example, the duration of the inhalation period is determined by sensing the flow rate of the inhalant, and the pulse delay period is automatically set to 20% of the inhalation period. Consequently, the pulse delivery period can be set to 60% of the inhalation period, and the pulse cessation period is the remaining 20% of the inhalation period. The number of pulses, namely the pulse-on and pulse-off periods, can be set similarly according to the duration of the pulse delivery period. For example, the number of pulses can be set to one, namely a pulse that spans the entire duration of the pulse delivery period. This example may be suitable for a subject experiencing shortness of breath or any difficulty in respiration. Alternatively, in cases where the subject is breathing normally, the pulse-on period is set to 200-300 milliseconds (ms), and the pulse-off period is set to 100 ms, while the number of pulses is automatically set by the duration of pulse delivery period which is derived from the measured inhalation period.

In some embodiments, the pulse delay period ranges from 0 ms to 2500 ms. Alternatively, in some embodiments, the pulse delay period ranges from 0% to 80% of the inhalation period.

In some embodiments, the pulse cessation period ranges from 0 ms to 2500 ms. Alternatively, in some embodiments, the pulse cessation period ranges from 80% to 0% of the inhalation period.

In some embodiments, each the pulse-on periods individually ranges from 100 ms to 5000 ms. Alternatively, each the pulse-on periods individually ranges from 10% to 100% of the inhalation period.

In some embodiments, each the pulse-off period individually ranges from 0 ms to 2500 ms. Alternatively, each the pulse-off periods individually ranges from 0% to 200% of the pulse-on period.

In some embodiments, the method is based on a single pulse per inhalation period. In some embodiments, the single pulse is effected such that the pulse delivery period starts essentially as the inhalation period starts (pulse delay period is essentially zero), and ends essentially as the inhalation period ends (pulse cessation period is essentially zero). In other embodiments the method is effected by using a single pulse that starts after the inhalation period starts, and ends before the inhalation to ends.

In some embodiments, the coordination of pulse delivery is set to deliver more than one pulse in succession during the pulse delivery period, until the device senses a decrease in the rate of intake close to the end of the inhalation period. In such embodiments, the device is set to interrupt each pulse-on period with a pulse-off period. In some embodiments, the device is set to deliver a predetermined number of pulses that ranges from 1 to 2, from 1 to 3, from 1 to 4, from 1 to 5, from 1 to 6, from 1 to 7, from 1 to 8, from 1 to 9, from 1 to 10, or from 1 to any number of pulses that can take place within the pulse delivery period as determined by any given breathing cycle. It is further noted that each of the pulses may span a different pulse-on period and be interrupted by a pulse-off period of different lengths.

The concentration of NO in the gNO-containing gaseous mixture is controlled by the concentration of NO is introduced into the inhalant, the output by which NO is introduced into the inhalant, the duration of the pulse-on period and the number of pulses introduced into the inhalant during the pulse delivery period. According to some embodiments of the present invention, during the pulse delivery period the inhalant is essentially a gNO-containing gaseous mixture which contains at least 160 ppm gNO, or a load of 80 ppm-hour per cycle, while during the pulse delay period and the pulse cessation period the inhalant is essentially devoid of gNO.

According to some embodiments, the method is effected by using more than one pulse, wherein the inhalant, which is produced by each of the pulses, delivers to the patient a different concentration of NO. For example, the method may be carried out by administering to the patient, during the pulse delivery period, three pulses, such that the inhalant that stems from the first pulse is characterized by an NO concentration of 160 ppm, the inhalant that stems from the second pulse is characterized by an NO concentration of 80 ppm, and the inhalant that stems from the first pulse is characterized by an NO concentration of 100 ppm. Hence, at least one pulse effects a concentration of at least 160 ppm. In other examples, some of the pulses may deliver an inhalant characterized by an NO concentration of more than 160 ppm.

Alternatively, the number of pulses, the concentration of NO in each of the pulses, and the duration of the first time period during which pulses are generated, are configured to deliver a gNO load per cycle of 80 ppm-hour.

As presented hereinabove, breathing cycle-coordinated pulse delivery inhalation allows the introduction of high concentrations of NO essentially during the periods of time in which the subject inhales at the highest in-breathing rate, thereby minimizing exposure of parts of the respiratory tract to high concentrations of NO. For example, since NO is introduced in pulses after the beginning of the inhalation period and before the end of the inhalation period, parts of the upper respiratory tract, the trachea and the some of the respiratory tree in the lungs which are not rich with alveolor capillaries, are only briefly exposed to high concentrations of NO due to the rate of inhalant intake, while the alveoli are exposed to this high concentrations of NO for a longer period of time.

An exemplary breathing cycle-coordinated pulse delivery inhalation scheme, according to some embodiments of the present invention, which exhibits three pulses during the pulse delivery period, is illustrated in FIG. 1 and FIG. 2.

FIG. 1 presents breathing cycle-coordinated pulse delivery inhalation scheme 10, showing inhalant flow curve 112 and NO concentration curve 114 on a common time scale, wherein breathing cycle period 116 comprises inhalation period 118, during which NO is delivered, and exhalation period 119, during which NO is not used. As can be seen in FIG. 1, NO is delivered after pulse delay period 120 such that the concentration of NO, as determined in the inhalant, is maximal NO concentration 124, and continues to be delivered in one or more pulses during pulse delivery period 121, and ends with pulse cessation period 122.

FIG. 2 presents a zoom-in view of breathing cycle-coordinated pulse delivery inhalation scheme 10 spanning inhalation period 118, wherein pulse delivery period 121 comprises three pulses, each spanning pulse-on period 130, interrupted by pulse-off period 131.

In some embodiments, the method is effected while monitoring various physiological parameters in the subject, as described herein.

The human subject can be subjected to the inhalation by active or passive means.

By "active means" it is meant that the gaseous mixture is administered or delivered to the respiratory tract of the human subject. This can effected, for example, by means of an inhalation device, such as a breathing cycle-coordinated pulse delivery inhalation device, having a delivery interface adapted for human respiratory organs. For example, the delivery interface can be placed intermittently on the human subject's respiratory organs, whereby when it is removed, the subject breaths ambient air or any other gaseous mixture that is devoid of gNO, as defined herein.

By "passive means" it is meant that the human subject inhales a gaseous mixture containing the indicated dose of gNO without devices for delivering the gaseous mixture to the respiratory tract.

In some embodiments, the method is carried out while maintaining a controlled mixture of inhaled and exhaled gases by standard means for monitoring and controlling, on-site, the contents and/or flow of the mixture to which the subject is subjected to, or that which is delivered through a delivery interface, and/or while monitoring on-site exhaled gases and controlling the intake by feedback in real-time. In some embodiments, the method is effected while monitoring the concentration of gNO, $FiO_2/O_2$, $ETCO_2$, and $NO_2$ in the gaseous mixture to which the subject is exposed or by monitoring other bodily systems non-invasively, such as blood oxygen saturation ($SpO_2/SaO_2/DO$) and the presence of methemoglobin in the blood (SpMet).

In some embodiments, the concentration of gNO in the gNO-containing gaseous mixture is controlled so as not to deviate from a predetermined concentration by more than 10%. For example, when the method is carried out while the concentration of gNO is set to 160 ppm, the method includes a check that the concentration of NO does not exceed margins of 144 ppm to 176 ppm.

Similarly, the $NO_2$ content in a gNO-containing gaseous mixture is controlled such that the concentration of $NO_2$ is maintained lower than 5 ppm.

Further, oxygen level in the gNO-containing gaseous mixture is controlled such that the concentration of $O_2$ in the mixture ranges from about 20% to about 25%.

Alternatively or in addition, the oxygen level in the gNO-containing gaseous mixture is controlled such that the fraction of inspired oxygen ($FiO_2$) ranges from about 20% to about 100%.

The phrase "fraction of inspired oxygen" or "$FiO_2$", as used herein, refers to the fraction or percentage of oxygen in a given gas sample. For example, ambient air at sea level includes 20.9% oxygen, which is equivalent to $FiO_2$ of 0.21. Oxygen-enriched air has a higher $FiO_2$ than 0.21, up to 1.00, which means 100% oxygen. In the context of embodiments of the present invention, $FiO_2$ is kept under 1 (less than 100% oxygen).

The phrase "end tidal $CO_2$" or "$ETCO_2$", as used herein, refers to the partial pressure or maximal concentration of carbon dioxide ($CO_2$) at the end of an exhaled breath, which is expressed as a percentage of $CO_2$ or the pressure unit mmHg Normal values for humans range from 5% to 6% $CO_2$, which is equivalent to 35-45 mmHg Since $CO_2$ diffuses out of the lungs into the exhaled air, $ETCO_2$ values reflect cardiac output (CO) and pulmonary blood flow as the gas is transported by the venous system to the right side of the heart and then pumped to the lungs by the right ventricles. A device called capnometer measures the partial pressure or maximal concentration of $CO_2$ at the end of exhalation. In the context of embodiments of the present invention, a capnometer is used and $ETCO_2$ levels are monitored so as to afford a warning feedback when $ETCO_2$ is more than 60 mmHg.

Levels of respiratory NO, $NO_2$ and $O_2$ concentration levels (both inhaled and exhaled; inspiratory and expiratory gases) are typically monitored continuously by sampling from a mouthpiece sample port located in an inhalation mask NO, $NO_2$ and $O_2$ equipped with an electrochemical analyzer. In the context of embodiments of the present invention, safety considerations requires the absolute minimization of the number of occasions in which $NO_2$ levels exceed 5 ppm, gNO concentration variations exceeding 10%, and $FiO_2/O_2$ levels drop below 20% during gNO administration.

In some embodiments, the method is effected while monitoring one or more physiological parameters in the subject and while assuring that no substantial change is effected in the monitored parameters.

In some embodiments, monitoring the one or more physiological parameters is effected by noninvasive measures and/or mild invasive measures.

In some embodiments, monitoring the physiological parameter(s) in the subject is effected by on-site measurement and analysis techniques based on samples collected sporadically, continuously or periodically from the subject on-site in real-time at the subject's bed-side, and/or off-site measurement and analysis techniques to based on samples collected sporadically or periodically from the subject which are sent for processing in a off-site which provides the results and analysis at a later point in time.

In the context of some embodiments of the present invention, the phrase "on-site measurement and analysis techniques" or "on-site techniques", refers to monitoring techniques that inform the practitioner of a given physiological parameter of the subject in real-time, without the need to send the sample or raw data to an off-site facility for analysis. On-site techniques are often noninvasive, however, some rely on sampling from an invasive medical device such as a respiratory tubus, a drainer tube, an intravenous catheter or a subcutaneous port or any other implantable probe. Thus, the phrase "on-site parameters", as used herein, refers to physiological parameters which are obtainable by online techniques.

Other that the trivial advantage of real-time on-site determination of physiological parameters, expressed mostly in the ability of a practitioner to respond immediately and manually to any critical change thereof, the data resulting from real-time online determination of physiological parameters can be fed into the machinery and be used for real-time feedback controlling of the machinery. In the context of embodiments of the present invention, the term "real-time" also relates to systems that update information and respond thereto substantially at the same rate they receive the information. Such real-time feedback can be used to adhere to the treatment regimen and/or act immediately and automatically in response to any critical deviations from acceptable parameters as a safety measure.

Hence, according to embodiments of the present invention, the term "on-site parameter" refers to physiological and/or mechanical and/or chemical datum which is obtainable and can be put to use or consideration at or near the subject's site (e.g., bed-side) in a relatively short period of time, namely that the time period spanning the steps of sampling, testing, processing and displaying/using the datum is relatively short. An "on-site parameter" can be obtainable, for example, in less than 30 minutes, less than 10 minutes, less than 5 minutes, less than 1 minute, less than 0.5 minutes, less than 20 seconds, less than 10 seconds, less than 5 seconds, or less than 1 second from sampling to use. For example, the time period required to obtain on-site parameters by a technique known as pulse oximetry is almost instantaneous; once the device is in place and set up, data concerning, e.g., oxygen saturation in the periphery to of a subject, are available in less than 1 second from sampling to use.

In the context of some embodiments of the present invention, the phrase "off-site measurement and analysis techniques" or "off-site techniques", refers to techniques that provide information regarding a given physiological parameter of the subject after sending a sample or raw data to an offline, and typically off-site facility, and receiving the analysis offline, sometimes hours or days after the sample had been obtained. Off-site techniques are oftentimes based on samples collected by mild invasive techniques, such as blood extraction for monitoring inflammatory cytokine plasma level, and invasive techniques, such as biopsy, catheters or drainer tubus, however, some off-site techniques rely on noninvasive sampling such as urine and stool chemistry offline and off-site analyses. The phrase "off-site parameters", as used herein, refers to physiological parameters which are obtainable by off-site laboratory techniques.

Hence, according to embodiments of the present invention, the term "off-site parameter" refers to physiological and/or mechanical and/or chemical datum which is obtain and can be put to use or consideration in a relatively long period of time, namely that the time period spanning the steps of sampling, testing, processing and displaying/using the datum is long compared to on-site parameters. Thus, an "off-site parameter" is obtainable in more than 1 day, more than 12 hours, more than 1 hour, more than 30 minutes, more than 10 minutes, or more than 5 minutes from sampling to use.

An "off-site parameter" is typically obtainable upon subjecting a sample to chemical, biological, mechanical or other procedures, which are typically performed in a laboratory and hence are not performed "on-site", namely by or near the subject's site.

Noninvasive measures for monitoring various physiological parameters include, without limitation, pulse oximetry, nonintubated respiratory analysis and/or capnometry. Mild invasive measures for monitoring various physiological parameters include, without limitation, blood extraction, continuous blood gas and metabolite analysis, and in some embodiments intubated respiratory analysis and transcutaneous monitoring measures.

The term "pulse oximetry" refers to a noninvasive and on-site technology that measures respiration-related physiological parameters by following light absorption characteristics of hemoglobin through the skin (finger, ear lobe etc.), and on the spectroscopic differences observed in oxygenated and deoxygenated species of hemoglobin, as well as hemoglobin species bound to other molecules, such as carbon monoxide (CO), and methemoglobin wherein the iron in the heme group is in the $Fe^{3+}$ (ferric) state. Physiological parameters that can be determined by pulse oximetry include $SpO_2$, SpMet and SpCO.

The phrase "nonintubated respiratory analysis", as used herein, refers to a group of noninvasive and on-site technologies, such as spirometry and capnography, which provide measurements of the physiological pulmonary mechanics and respiratory gaseous chemistry by sampling the inhaled/exhaled airflow or by directing subject's breath to a detector, all without entering the subject's respiratory tract or other orifices nor penetrating the skin at any stage.

The term "spirometry" as used herein, refers to the battery of measurements of respiration-related parameters and pulmonary functions by means of a noninvasive and on-site spirometer. Following are exemplary spirometry parameters which may be used in the context of some embodiments of the present invention:

The spirometric parameter Tidal volume (TV) is the amount of air inhaled and exhaled normally at rest, wherein normal values are based on person's ideal body weight.

The spirometric parameter Total Lung Capacity (TLC) is the maximum volume of air present in the lungs.

The spirometric parameter Vital Capacity (VC) is the maximum amount of air that can expel from the lungs after maximal inhalation, and is equal to the sum of inspiratory reserve volume, tidal volume, and expiratory reserve volume.

The spirometric parameter Slow Vital Capacity (SVC) is the amount of air that is inhaled as deeply as possible and then exhaled completely, which measures how deeply a person can breathe.

The spirometric parameter Forced Vital Capacity (FVC) is the volume of air measured in liters, which can forcibly be blown out after full inspiration, and constitutes the most basic maneuver in spirometry tests.

The spirometric parameter Forced Expiratory Volume in the 1st second (FEV1) is the volume of air that can forcibly be blown out in one second, after full inspiration. Average values for FEV1 in healthy people depend mainly on sex and age, whereas values falling between 80% and 120% of the average value are considered normal. Predicted normal values for FEV1 can be calculated on-site and depend on age, sex, height, weight and ethnicity as well as the research study that they are based on.

The spirometric parameter FEV1/FVC ratio (FEV1%) is the ratio of FEV1 to FVC, which in healthy adults should be approximately 75-80%. The predicted FEV1% is defined as FEV1% of the patient divided by the average FEV1% in the appropriate population for that person.

The spirometric parameter Forced Expiratory Flow (FEF) is the flow (or speed) of air coming out of the lung during the middle portion of a forced expiration. It can be given at discrete times, generally defined by what fraction remains of the forced vital capacity (FVC), namely 25% of FVC (FEF25), 50% of FVC (FEF50) or 75% of FVC (FEF75). It can also be given as a mean of the flow during an interval, also generally delimited by when specific fractions remain of FVC, usually 25-75% (FEF25-75%). Measured values ranging from 50-60% up to 130% of the average are considered normal, while predicted normal values for FEF can be calculated on-site and depend on age, sex, height, weight and ethnicity as well as the research study that they are based on. Recent research suggests that FEF25-75% or FEF25-50% may be a more sensitive parameter than FEV1 in the detection of obstructive small airway disease. However, in the absence of concomitant changes in the standard markers, discrepancies in mid-range expiratory flow may not be specific enough to be useful, and current practice guidelines recommend continuing to use FEV1, VC, and FEV1/VC as indicators of obstructive disease.

The spirometric parameter Negative Inspiratory Force (NIF) is the greatest force that the chest muscles can exert to take in a breath, wherein values indicate the state of the breathing muscles.

The spirometric parameter MMEF or MEF refers to maximal (mid-)expiratory flow and is the peak of expiratory flow as taken from the flow-volume curve and measured in liters per second. MMEF is related to peak expiratory flow (PEF), which is generally measured by a peak flow meter and given in liters per minute.

The spirometric parameter Peak Expiratory Flow (PEF) refers to the maximal flow (or speed) achieved during the maximally forced expiration initiated at full inspiration, measured in liters per minute.

The spirometric parameter diffusing capacity of carbon monoxide ($D_LCO$) refers to the carbon monoxide uptake from a single inspiration in a standard time (usually 10 sec). On-site calculators are available to correct $D_LCO$ for hemoglobin levels, anemia, pulmonary hemorrhage and altitude and/or atmospheric pressure where the measurement was taken.

The spirometric parameter Maximum Voluntary Ventilation (MVV) is a measure of the maximum amount of air that can be inhaled and exhaled within one minute. Typically this parameter is determined over a 15 second time period before being extrapolated to a value for one minute expressed as liters/minute. Average values for males and females are 140-180 and 80-120 liters per minute respectively.

The spirometric parameter static lung compliance (Cst) refers to the change in lung volume for any given applied pressure. Static lung compliance is perhaps the most sensitive parameter for the detection of abnormal pulmonary mechanics. Cst is considered normal if it is 60% to 140% of the average value of a commensurable population.

The spirometric parameter Forced Expiratory Time (FET) measures the length of the expiration in seconds.

The spirometric parameter Slow Vital Capacity (SVC) is the maximum volume of air that can be exhaled slowly after slow maximum inhalation.

Static intrinsic positive end-expiratory pressure (static PEEPi) is measured as a plateau airway opening pressure during airway occlusion.

The spirometric parameter Maximum Inspiratory Pressure (MIP) is the value representing the highest level of negative pressure a person can generate on their own during an inhalation, which is expresented by centimeters of water pressure ($cmH_2O$) and measured with a manometer and serves as n indicator of diaphragm strength and an independent diagnostic parameter.

The term "capnography" refers to a technology for monitoring the concentration or partial pressure of carbon dioxide ($CO_2$) in the respiratory gases. End-tidal $CO_2$, or $ETCO_2$, is the parameter that can be determined by capnography.

Gas detection technology is integrated into many medical and other industrial to devices and allows the quantitative determination of the chemical composition of a gaseous sample which flows or otherwise captured therein. In the context of embodiments of the present invention, such chemical determination of gases is part of the on-site, noninvasive battery of tests, controlled and monitored activity of the methods presented herein. Gas detectors, as well as gas mixers and regulators, are used to determine and control parameters such as fraction of inspired oxygen level ($FiO_2$) and the concentration of nitric oxide in the inhaled gas mixture.

According to some embodiments of the present invention, the measurement of vital signs, such as heart rate, blood pressure, respiratory rate and a body temperature, is regarded as part of a battery of on-site and noninvasive measurements.

The phrase "integrated pulmonary index", or IPI, refers to a patient's pulmonary index which uses information on inhaled/exhaled gases from capnography and on gases dissolved in the blood from pulse oximetry to provide a single value that describes the patient's respiratory status. IPI, which is obtained by on-site and noninvasive techniques, integrates four major physiological parameters provided by a patient monitor (end-tidal $CO_2$ and respiratory rate as measured by capnography, and pulse rate and blood oxygenation $SpO_2$ as measured by pulse oximetry), using this information along with an algorithm to produce the IPI score. IPI provides a simple indication in real time (on-site) of the patient's overall ventilatory status as an integer (score) ranging from 1 to 10. IPI score does not replace current patient respiratory parameters, but used to assess the patient's respiratory status quickly so as to determine the need for additional clinical assessment or intervention.

According to some of any of the embodiments described herein, the monitored physiological or chemical parameters include one or more of the following parameters:

a methemoglobin level (SpMet) (an on-line parameter);

an end-tidal $CO_2$ level ($ETCO_2$) (an on-line parameter);

an oxygenation level/$FIO_2$ or oxygen saturation level ($SpO_2$) (an on-line parameter);

an inflammatory cytokine plasma level (an off-line parameter); and a serum nitrite/nitrate level ($NO_2^-/NO_3^-$) (an off-line parameter).

According to some of any of the embodiments described herein, the monitored physiological or chemical parameters further include one or more of the following parameters:

a urine level of nitrogen dioxide (urine nitrite level) (an off-line parameter);

a vital sign selected from the group consisting of a heart rate, a blood pressure, a respiratory rate and a body temperature (an on-line parameter);

a pulmonary function (spirometric parameter) (an on-line parameter) such as, but not limited to, forced expiratory volume ($FEV_1$), maximum mid-expiratory flow (MMEF), diffusing capacity of the lung for carbon monoxide ($D_LCO$), forced vital capacity (FVC), total lung capacity (TLC) and residual volume (RV);

a hematological marker (an off-line parameter), such as, but not limited to, a hemoglobin level, a hematocrit ratio, a red blood cell count, a white blood cell count, a white blood cell differential and a platelet count;

a coagulation parameter (an off-line parameter) such as, but not limited to, a prothrombin time (PT), a prothrombin ratio (PR) and an international normalized ratio (INR);

a serum creatinine level (an off-line parameter);

a liver function marker (an off-line parameter) selected from the group consisting of a aspartate aminotransferase (AST) level, a serum glutamic oxaloacetic transaminase (SGOT) level, an alkaline phosphatase level, and a gamma-glutamyl transferase (GGT) level;

a vascular endothelial activation factor (an off-line parameter) selected from the group consisting of Ang-1, Ang-2 and Ang-2/Ang-1 ratio.

Non-limiting examples of inflammatory cytokines include (TNF)α, (IL)-1β, IL-6, IL-8, IL-10 and IL-12p70.

According to some embodiments of the present invention, the method as disclosed herein is such that no substantial change in at least one of the monitored parameters is observed.

In the context of the present embodiments, a change in a parameter is considered substantial when a value of an observation (measurement, test result, reading, calculated result and the likes) or a group of observations falls notably away from a normal level, for example falls about twice the upper limit of a normal level.

A "normal" level of a parameter is referred to herein as baseline values or simply "baseline". In the context of the present embodiments, the term "baseline" is defined as a range of values which have been determined statistically from a large number of observations and/or measurements which have been collected over years of medical practice with respect to the general human population, a specific sub-set thereof (cohort) or in some cases with respect to a specific person. A baseline is a parameter-specific value which is generally and medically accepted in the art as normal for a subject under certain physical conditions. These baseline or "normal" values, and means of determining these normal values, are known in the art. Alternatively, a baseline value may be determined from or in a specific subject before effecting the method described herein using well known and accepted methods, procedures and technical means. A baseline is therefore associated with a range of tolerated values, or tolerance, which have been determined in conjunction with the measurement of a parameter. In other words, a baseline is a range of acceptable values which limit the range of observations which are considered as "normal". The width of the baseline, or the difference between the upper and lower limits thereof are referred to as the "baseline range", the difference from the center of the range is referred to herein as the "acceptable deviation unit" or ADU. For example, a baseline of 4-to-8 has a baseline range of 4 and an acceptable deviation unit of 2.

In the context of the present embodiments, a significant change in an observation pertaining to a given parameter is one that falls more than 2 acceptable deviation unit (2 ADU) from a predetermined acceptable baseline. For example, an observation of 10, pertaining to a baseline of 4-to-8 (characterized by a baseline range of 4, and an acceptable deviation unit of 2), falls one acceptable deviation unit, or 1 AUD from baseline. Alternatively, a change is regarded substantial when it is more than 1.5 ADU, more than 1 ADU or more than 0.5 ADU.

In the context of the present embodiments, a "statistically significant observation" or a "statistically significant deviation from a baseline" is such that it is unlikely to have occurred as a result of a random factor, error or chance.

It is noted that in some parameters or groups of parameters, the significance of a change thereof may be context-dependent, biological system-dependent, medical case-dependent, human subject-dependent, and even measuring machinery-dependent, namely a particular parameter may require or dictate stricter or looser criteria to to determine if a reading thereof should be regarded as significant. It is noted herein that in specific cases some parameters may not be measurable due to patient condition, age or other reasons. In such cases the method is effected while monitoring the other parameters.

A deviation from a baseline is therefore defined as a statistically significant change in the value of the parameter as measured during and/or following a full term or a part term of administration the regimen described herein, compared to the corresponding baseline of the parameter. It is noted herein that observations of some parameters may fluctuate for several reasons, and a determination of a significant change therein should take such events into consideration and correct the appropriate baseline accordingly.

Monitoring methemoglobin and serum nitrite levels has been accepted in the art as a required for monitoring the safety of gNO inhalation in a subject. Yet, to date, no clear indication that methemoglobin and serum nitrite levels remain substantially unchanged upon gNO inhalation by a human subject.

According to some embodiments of the present invention, the method comprises monitoring at least one of the parameters described hereinabove.

According to some embodiments, the monitored parameter is methemoglobin level.

As methemoglobin levels can be measured using noninvasive measures, the parameter of percent saturation at the periphery of methemoglobin (SpMet) is used to monitor the stability, safety and effectiveness of the method presented herein. Hence, according to some embodiments of the present invention, the followed parameter is SpMet and during and following the administration, the SpMet level does not exceed 5%, and preferably does not exceed 1%.

According to some embodiments, the monitored parameter is serum nitrate/nitrite level.

High nitrite and nitrate levels in a subject's serum are associated with NO toxicity and therefore serum nitrite/nitrate levels are used to detect adverse effects of the method presented herein. According to some embodiments of the present invention, the tested parameter is serum nitrite/nitrate, which is monitored during and following the treatment and the acceptable level of serum nitrite is less than 2.5 to micromole/liter and serum nitrate is less than 25 micromole/liter.

According to some embodiments, the monitored parameter is level of inflammatory markers.

An elevation of inflammatory markers is associated with a phenomenon called "cytokine storm", which has been observed in subjects undergoing gNO inhalation treatment.

Monitoring inflammatory markers while performing the method as described herein has never been taught heretofore. Moreover, methods involving gNO inhalation at a regimen in which no significant change in inflammatory markers is observed have never been taught heretofore.

According to some embodiments, the method comprises monitoring at least two of the above-mentions parameters.

In some of these embodiments, the monitored parameters are two or all of methemoglobin level, serum nitrite level and inflammatory markers.

While changes in methemoglobin level, serum nitrite level and inflammatory markers are typically observed in subjects subjected to gNO inhalation, the findings that no substantial change in these parameters has been observed in human subjects undergoing the disclosed regimen are surprising.

Hence, according to some embodiments of the present invention, the method as disclosed herein is carried out while monitoring the methemoglobin level (SpMet), the serum nitrite level ($NO_2^-$) and a group of inflammatory cytokine plasma level, such as, but not limited to, (TNF)α, (IL)-1β, IL-6, IL-8, IL-10 and IL-12p70 serum levels in the subject, wherein a change in at least one of these parameters is less than 2 acceptable deviation units from a baseline.

According to some of any of the embodiments described herein, the method is effected while monitoring at least one, at least two, or all on-site parameters which include SpMet, $SpO_2$ and $ETCO_2$, and/or monitoring at least one or all off-site parameters which include serum nitrite/nitrate level and inflammatory cytokines in the plasma.

For example, the method is effected while monitoring SpMet as an on-site parameter. Alternatively, the method is effected while monitoring SpMet and $ETCO_2$ as on-site parameters. Alternatively, the method is effected while monitoring SpMet, $ETCO_2$ and $SpO_2$ as on-site parameters.

Further alternatively, the method is effected while monitoring SpMet as one on-site parameter, and inflammatory cytokines in the plasma as one off-site parameter. Alternatively, the method is effected while monitoring SpMet and $ETCO_2$ as on-site parameters, and serum nitrite/nitrate level as one off-site parameter. Alternatively, the method is effected while monitoring SpMet as one on-site parameter, and inflammatory cytokines in the plasma and serum nitrite/nitrate level as off-site parameters. Alternatively, the method is effected while monitoring $ETCO_2$ as one on-site parameter, and inflammatory cytokines in the plasma and serum nitrite/nitrate level as off-site parameters. Alternatively, the method is effected while monitoring $SpO_2$ as one on-site parameter, and inflammatory cytokines in the plasma and serum nitrite/nitrate level as off-site parameters.

Further alternatively, the method is effected while monitoring SpMet, $ETCO_2$ and $SpO_2$ as on-site parameters, and inflammatory cytokines in the plasma and serum nitrite/nitrate level as off-site parameters.

According to some of any of the embodiments described herein, the method is effected while monitoring at least one, at least two, or all on-site parameters which include SpMet, $SpO_2$ and $ETCO_2$, and/or monitoring at least one or all off-site parameters which include serum nitrite/nitrate level and inflammatory cytokines in the plasma, and further monitoring one or more and in any combination of:

a urine $NO_2$ level (an off-line parameter);
a vital sign (an on-line parameter);
a pulmonary function (an on-line parameter);
a hematological marker (an off-line parameter);
a coagulation parameter (an off-line parameter);
a serum creatinine level (an off-line parameter);
a liver function marker (an off-line parameter);
a vascular endothelial activation factor (an off-line parameter).

According to some of any of the embodiments described herein, the method is effected while monitoring at least one, at least two, or all on-site chemical parameters in the inhaled gas mixture, such as $FiO_2$ and $NO_2$.

It is noted herein that for any of the abovementioned embodiments, that the method is effected while no substantial change is observed in any one or more than one or all of the monitored parameters described herein.

According to some embodiments of the present invention, the method is effected while monitoring urine nitrite levels, such that the urine nitrite level is substantially unchanged during and subsequent to carrying out the method as presented herein. It is noted herein that urine nitrite levels may fluctuate for several known reasons, and a determination of a significant change therein should take such events into consideration and correct the appropriate baseline accordingly.

It is noted that urine nitrite level is indicative for the safety of gNO inhalation, yet, has never been monitored heretofore in the context of intermittent breathing cycle-coordinated pulse delivery inhalation of gNO as disclosed herein.

According to some embodiments of the present invention, hematological markers, such as the hemoglobin level, the hematocrit ratio, the red blood cell count, the white blood cell count, the white blood cell differential and the platelet count, are substantially unchanged during and subsequent to carrying out the method as presented herein.

According to some embodiments of the present invention, vascular endothelial activation factors, such as Ang-1, Ang-2 and Ang-2/Ang-1 ratio, as well as the serum creatinine level and various liver function markers, such as the aspartate aminotransferase (AST) level, the serum glutamic oxaloacetic transaminase (SGOT) level, the alkaline phosphatase level, and the gamma-glutamyl transferase (GGT) level, are substantially unchanged during and subsequent to carrying out the method as presented herein.

Oxygenation of the subject can be assessed by measuring the subject's saturation of peripheral oxygen ($SpO_2$). This parameter is an estimation of the oxygen saturation level, and it is typically measured using noninvasive measures, such as a pulse oximeter device. Hence, according to some embodiments of the present invention, the followed parameter during and following the administration is $SpO_2$, and the level of $SpO_2$ is higher than about 89%.

According to some embodiments of the present invention, various vital signs, such as the heart rate, the blood pressure, the respiratory rate and the body temperature; and/or various pulmonary functions (spirometric parameter), such as forced expiratory volume ($FEV_1$), maximum mid-expiratory flow (MMEF), diffusing capacity of the lung for carbon monoxide ($D_LCO$), forced vital capacity (FVC), total lung capacity (TLC) and residual volume (RV); and various coagulation parameters, to such as the prothrombin time (PT), the prothrombin ratio (PR) and the international normalized ratio (INR), are substantially unchanged during and subsequent to carrying out the method as presented herein. It is noted that these parameters are regarded as an indication that the general health of the subject is not deteriorating as a result of the medical condition and/or the treatment.

According to some embodiments, the aforementioned general health indicators show an improvement during and subsequent to carrying out the method as presented herein, indicating that the treatment is beneficial to the subject.

Thus, according to some embodiments of the present invention, the method as disclosed herein is effected such that general health indicators as described herein are at least remained unchanged or are improved.

According to some embodiments of the present invention, a human subject in need of gNO inhalation treatment is a human that suffers from a disease or disorder of the respiratory tract.

As used herein, the phrase "respiratory tract" encompasses all organs and tissues that are involved in the process of respiration in a human subject or other mammal subject, including cavities connected to the respiratory tract such as ears and eyes.

A respiratory tract, as used herein, encompasses the upper respiratory tract, including the nose and nasal passages, prenasal sinuses, pharynx, larynx, trachea, bronchi, and nonalveolar bronchioles; and the lower respiratory tract, including the lungs and the respiratory bronchioles, alveolar ducts, alveolar sacs, and alveoli therein.

Respiratory diseases and disorders which are treatable by any of the methods presented herein, can be classified as: Inflammatory lung disease; Obstructive lung diseases such as COPD; Restrictive lung diseases; Respiratory tract infections, such as upper/lower respiratory tract infections, and malignant/benign tumors; Pleural cavity diseases; pulmonary vascular diseases; and Neonatal diseases.

According to embodiments of the present invention, restrictive diseases include intrinsic restrictive diseases, such as asbestosis caused by long-term exposure to asbestos dust; radiation fibrosis, usually from the radiation given for cancer treatment; certain drugs such as amiodarone, bleomycin and methotrexate; as a to consequence of another disease such as rheumatoid arthritis; hypersensitivity pneumonitis due to an allergic reaction to inhaled particles; acute respiratory distress syndrome (ARDS), a severe lung condition occurring in response to a critical illness or injury; infant respiratory distress syndrome due to a deficiency of surfactant in the lungs of a baby born prematurely; idiopathic pulmonary fibrosis; idiopathic interstitial pneumonia, of which there are several types; sarcoidosis; eosinophilic pneumonia; lymphangioleiomyomatosis; pulmonary Langerhans' cell histiocytosis; pulmonary alveolar proteinosis; interstitial lung diseases (ILD) such as inhaled inorganic substances: silicosis, asbestosis, berylliosis, inhaled organic substances: hypersensitivity pneumonitis, drug induced: antibiotics, chemotherapeutic drugs, antiarrhythmic agents, statins, connective tissue disease: Systemic sclerosis, polymyositis, dermatomyositis, systemic lupus erythematosus, rheumatoid arthritis, infection, atypical pneumonia, *pneumocystis* pneumonia (PCP), tuberculosis, *chlamydia trachomatis*, RSV, idiopathic sarcoidosis, idiopathic pulmonary fibrosis, Hamman-Rich syndrome, antisynthetase syndrome, and malignant lymphangitic carcinomatosis; and extrinsic restrictive diseases, such as neuromuscular diseases, including Myasthenia gravis and Guillain bane; nonmuscular diseases of the upper thorax such as kyphosis and chest wall deformities; diseases restricting lower thoracic/abdominal volume due to obesity, diaphragmatic hernia, or the presence of ascites; and pleural thickening.

According to embodiments of the present invention, obstructive diseases include asthma, COPD, chronic bronchitis, emphysema, bronchiectasis, CF, and bronchiolitis.

Respiratory diseases and disorders which are treatable by any of the methods presented herein, can also be classified as acute or chronic; caused by an external factor or an endogenous factor; or as infectious or noninfectious respiratory diseases and disorders.

Diseases and disorders of the respiratory tract include otolaryngological and/or an upper respiratory tract and/or a lower respiratory system diseases and disorders, and are also referred to herein as "respiratory diseases" or "respiratory diseases and disorders".

Exemplary, and most common, diseases and disorders of the respiratory tract to include acute infections, such as, for example, sinusitis, broncholitis, tuberculosis, pneumonia, bronchitis, and influenza, and chronic conditions such as asthma, CF and chronic obstructive pulmonary disease.

According to some embodiments of the present invention, subject in need of gNO inhalation treatment is a human subject that suffers from a disease or disorder that is manifested in the respiratory tract, as defined herein.

In any of the embodiments described herein a human subject includes any living human at any age, from neonatals and newborns, to adults and elderly people, at any weight, height, and any other physical state.

A disease or disorder that is manifested in the respiratory tract encompasses also any disease or disorder that is not caused by an infection or airway obstruction in the respiratory tract, rather, is caused by another factor yet can be manifested by an infection or airway obstruction in the respiratory tract.

An exemplary such condition is cystic fibrosis (CF). CF is a genetic disorder in which mutations in the epithelial chloride channel, CF transmembrane conductance regulator (CFTR), impairs various mechanism of innate immunity.

Chronic microbial lung infections are the leading cause of morbidity and mortality in CF patients. Early antibiotic eradication treatment of CF patients for the most prevalent bacterial pathogen, *Pseudomonas aeruginosa*, has considerably increased the life expectancy in CF, however still the vast majority of adult CF patients suffer from chronic *P. aeruginosa* lung infections which are difficult to treat due to biofilm formation and the development of antibiotic resistant strains of the virulent. Other species found in CF airways include antibiotic resistant strains such as methicillin-resistant *S. aureus* (MRSA), members of the *Burkholderia cepacia* complex, *Haemophilus influenzae*, *Stenotrophomonas maltophilia*, *Achromobacter xylosoxidans*, non-tuberculous *mycobacteria* (NTM) species and various strict anaerobic bacteria.

According to some embodiments of the present invention, a human subject in need of gNO inhalation treatment is a human subject that is prone to suffer from a respiratory tract disease or disorder. By "prone to suffer" it is meant that the human subject is at a higher risk of suffering from the disease or disorder compared to a normal subject.

Such human subjects include, for example, immuno-compromised subjects such as subjects having HIV, cancer patients undergoing or which underwent to chemotherapy, cancer and other patients undergoing or which underwent transplantation, including bone marrow transplantation and transplantation of a solid organ, subjects with chronic asthma or sinusitis, and subjects which were in contact with subject(s) afflicted by an infectious respiratory tract disease or disorder, or which have otherwise been exposed to a pathogen. It is noted herein that subjecting a human subject prone to suffer from a respiratory tract disease or disorder to the gNO inhalation treatment presented herein, can be regarded as a preventative treatment, preventive care, or as a prophylactic medical treatment.

Alternatively, a human subject in need of gNO treatment is an immuno-compromised subject such as subjects having HIV, cancer patients undergoing or which underwent chemotherapy, cancer and other patients undergoing or which underwent transplantation, including bone marrow transplantation and transplantation of a solid organ, which have been infected or otherwise suffer from a respiratory disease or disorder as described herein.

Exemplary diseases or disorders of such immune-compromised subjects are described in more detail hereinbelow.

According to some embodiments of the present invention, a human subject in need of gNO inhalation treatment is a human subject that suffers from a disease or disorder that is treatable via the respiratory tract.

Since inhaled gNO is absorbed in the lungs, it contacts the blood system and hence can reach other tissues and organs in the biological system. Thus, diseases and disorders that are not associated directly to the respiratory tract, yet can be treated by inhalation of agents that show therapeutic effect on such diseases and disorders, can be treated according to embodiments of the present invention. Exemplary such diseases and disorders include, but are not limited to, acidosis, sepsis, leishmaniasis, and various viral infections.

Additional such diseases and disorders include viral infections.

The present inventors have contemplated that the use of supraphysiologic concentrations of gNO administered by intermittent breathing cycle-coordinated pulse delivery inhalation of gNO at concentrations of at least 160 ppm or an equivalent load thereof (e.g., 80 ppm-hour) may provide a broad spectrum, non-specific antiviral activity to be used at various stages of infection.

According to some embodiments of the present invention, a human in need of to gNO inhalation is a human afflicted by a disease or disorder that is treatable by gNO. The range of treatable diseases and disorders spans ophthalmological, otolaryngological and/or an upper respiratory tract and/or a lower respiratory system diseases and disorders, as well as systemic medical conditions.

Exemplary diseases and disorders treatable by gNO include, without limitation, a heparin-protamine reaction, a traumatic injury, a traumatic injury to the respiratory tract, acidosis or sepsis, acute mountain sickness, acute pulmonary edema, acute pulmonary hypertension, acute pulmonary thromboembolism, adult respiratory distress syndrome, an acute pulmonary vasoconstriction, aspiration or inhalation injury or poisoning, asthma or status asthmaticus, bronchopulmonary dysplasia, hypoxia or chronic hypoxia, chronic pulmonary hypertension, chronic pulmonary thromboembolism, cystic fibrosis (CF), Aspergilosis, aspergilloma, Cryptococcosis, fat embolism of the lung, haline membrane disease, idiopathic or primary pulmonary hypertension, inflammation of the lung, perinatal aspiration syndrome, persistent pulmonary hypertension of a newborn and post cardiac surgery.

According to some embodiments of the present invention, exemplary treatable diseases or disorders include, without limitation, a bacterial-, viral- and/or fungal bronchiolitis, a bacterial-, viral- and/or fungal pharyngitis and/or laryngotracheitis, a bacterial-, viral- and/or fungal pneumonia, a bacterial-, viral- and/or fungal pulmonary infection, a bacterial-, viral- and/or fungal sinusitis, a bacterial-, viral- and/or fungal upper and/or lower respiratory tract infection, a bacterial-, viral- and/or fungal-exacerbated asthma, a respiratory syncytial viral infection, bronchiectasis, bronchitis, chronic obstructive lung disease (COPD), cystic fibrosis (CF), Aspergilosis, aspergilloma, Cryptococcosis, emphysema, otitis, a bacterial-, viral- and/or fungal otitis externa, otitis media, conjunctivitis, uveitis primary ciliary dyskinesia (PCD) and pulmonary aspergillosis (ABPA).

According to some embodiments of the present invention, the disease or disorder treatable by gNO is associated with a pathogenic microorganism. The pathogenic microorganisms, according to some embodiments of the present invention, can be, for example, Gram-negative bacteria, Gram-positive bacteria, viruses and viable virions, fungi and parasites.

Exemplary pathogenic microorganisms include, but are not limited to, sp. *Acinetobacter baumarmii*, *Aspergillus niger*, *Bacteroides vulgatus*, *Burkholderia cepacia*, *Candida albicans*, *Clostridium perfringens*, Enteric Group 137, *Enterococcus faecium*, *Enterobacter aerogenes*, *Escherichia cofi*, *Klebsiella pneumoniae*, *Mycobacteria tuberculosis*, *Pasteurella multocida*, *Propionibacterium acnes*, *Propionibacteriumgranulosum*, *Proteus mirabilis*, *Providencia rusfigianii*, *Pseudomonas aeruginosa*, *Pseudomonas* sp., *Serratia marcesecens*, *Staphylococcus aureus*, *Staphylococcus aureus* (FVL positive), *Staphylococcus aureus* (VNL positive), *Staphylococcus aureus* MRSA, *Staphylococcus aureus* MRSA, *Staphylococcus aureus* MRSA, Streptococci Group B, Streptococci Group D, Streptococci Group G, *Streptococcipyrogenes* rosenbach Group A, *Streptococcus pneumoniae*, *Trichophyton meriagrophytes*, *Trichophyton rubrum*, and *Vibrio vuMucus*.

Exemplary Gram-negative bacteria include, but are not limited to, Proteobacteria, Enterobacteriaceae, sp. *Acinetobacter baumannii.*, *Bdellovibrio*, *Cyanobacteria*, *Enterobacter cloacae*, *Escherichia coli*, *Helicobacter*, *Helicobacter pylori*, *Hemophilus influenza*, *Klebsiella pneumonia*,

*Legionella, Legionella pneumophila, Moraxella, Moraxella catarrhalis, Neisseria gonorrhea, Neisseria meningitides, Proteus mirabilis, Pseudomonas, Pseudomonas aeruginosa, Salmonella, Salmonella enteritidis, Salmonella typhi, Serratia marcescens, Shigella, Spirochaetes* and *Stenotrophomonas*.

Exemplary Gram-positive bacteria include, but are not limited to, *Bacillus* species such as sp. *B. alcalophilus, B. alvei, B. aminovorans, B. amyloliquefaciens, B. aneurinolyticus, B. anthracis, B. aquaemaris, B. atrophaeus, B. boroniphilus, B. brevis, B. caldolyticus, B. centrosporus, B. cereus, B. circulans, B. coagulans, B. firmus, B. flavothermus, B. fusiformis, B. globigii, B. infernus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis* and *B. weihenstephanensis, Clostridium* species such as *C. acetobutylicum, C. aerotolerans, C. argentinense, C. baratii, C. beijerinckii, C. bifermentans, C. botulinum, C. butyricum, C. cadaveris, C. cellulolyticum, C. chauvoei, C. clostridioforme, C. colicanis, C. difficile, C. estertheticum, C. fallax, C. feseri, C. formicaceticum, C. histolyticum, C. innocuum, C. kluyveri, C. lavalense, C. ljungdahlii, C. novyi, C. oedematiens, C. paraputrificum, C. perfringens, C. phytofermentans, C. piliforme, C. ragsdalei, C. ramosum, C. scatologenes, C. septicum, C. sordellii, C. sporogenes, C. sticklandii, C. tertium, C. tetani, C. thermocellum, C. thermosaccharolyticum, C. tyrobutyricum, Corynebacterium* species such as *C. accolens, C. afermentans, C. amycolatum, C. aquaticum, C. argentoratense, C. auris, C. bovis, C. diphtheriae, C. equi, C. flavescens, C. glucuronolyticum, C. glutamicum, C. granulosum, C. haemolyticum, C. halofytica, C. jeikeium, C. macginleyi, C. matruchotii, C. minutissimum, C. parvum, C. propinquum, C. pseudodiphtheriticum, C. pseudotuberculosis, C. pyogenes, C. renale, C. spec, C. striatum, C. tenuis, C. ulcerans, C. urealyticum, C. urealyticum* and *C. xerosis, Listeriai* species such as *L. grayi, L. innocua, L. ivanovii, L. monocytogenes, L. murrayi, L. seeligeri* and *L. welshimeri, Staphylococcus* species such as *S. arlettae, S. aureus, S. auricularis, S. capitis, S. caprae, S. carnosus, S. chromogenes, S. cohnii, S. condimenti, S. delphini, S. devriesei, S. epidermidis, S. equorum, S. felis, S. fleurettii, S. gallinarum, S. haemolyticus, S. hominis, S. hyicus, S. intermedius, S. kloosii, S. leei, S. lentus, S. lugdunensis, S. lutrae, S. massiliensis, S. microti, S. muscae, S. nepalensis, S. pasteuri, S. pettenkoferi, S. piscifermentans, S. pseudintermedius, S. pseudolugdunensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri* and *S. xylosus,* and *Streptococcus* species such as *S. agalactiae, S. anginosus, S. bovis, S. canis, S. constellatus, S. dysgalactiae, S. equinus, S. iniae, S. intermedius, S. mitis, S. mutans, S. oralis, S. parasanguinis, S. peroris, S. pneumoniae, S. pyogenes, S. ratti, S. salivarius, S. sanguinis, S. sobrinus, S. suis, S. thermophilus, S. uberis, S. vestibularis, S. viridians* and *S. zooepidemicus*.

As discussed hereinabove, the disease or disorder which can be treated by effecting the method presented herein to a human subject, includes bacterial-, viral- and/or fungal bronchiolitis, bacterial-, viral- and/or fungal pharyngitis and/or laryngotracheitis, bacterial-, viral- and/or fungal sinusitis, bacterial-, viral- and/or fungal upper and/or lower respiratory tract infection, bacterial-, viral- and/or fungal-exacerbated asthma, bacterial-, viral-, fungal- and/or parasitic pneumonia, the common cold, cystic fibrosis related infections, aspergillosis, aspergilloma, respiratory syncytial viral infections, acidosis or sepsis, oral fungal infections, bronchitis, candidiasis of the oral cavity (thrush), canker sores, epiglottitis (supraglottitis), halitosis, herpes, laryngitis, laryngotracheitis, nasopharyngitis, otitis externa and otitis media, conjunctivitis, uveitis (and other eye infections) pharyngitis, pulmonary aspergillosis (ABPA), respiratory syncytial virus infections, rhinitis, rhinopharyingitis, rhinosinusitis, stomatitis, tonsillitis, tracheitis, tuberculosis, cryptococcosis and tympanitis.

According to some embodiments of the present invention, a human subject in need of gNO inhalation is a human subject in need of preemptive, preventative and prophylactic treatment of a disease or disorder as described herein. Hence, a subject not suffering from any current or manifested disease, and/or a subject that is suspected of being exposed to a pathogen, and/or a subject that suffers from one disease, is treated by the method(s) presented herein in order to prevent the occurrence of another disease or disorder.

According to an aspect of some embodiments of the present invention, there is provided a method of treating a human subject suffering from bronchiolitis, which is effected by subjecting the subject to intermittent breathing cycle-coordinated pulse delivery inhalation regimen, gNO at a concentration of at least 160 ppm, or at a load per cycle of 80 ppm-hour, thereby treating bronchiolitis.

It is noted herein that the treatable bronchiolitis, according to some embodiments of the present invention, can be associated with a pathogenic microorganism or not associated therewith. It is therefore noted that the method presented herein can be used to treat idiopathic bronchiolitis, bacterial- and/or viral-induced bronchiolitis and/or bronchiolitis that is associated with other medical conditions such as, but not limited to, immune deficiency.

In some embodiments, the bronchiolitis is a viral-induced bronchiolitis. Exemplary viral infections that are known to be manifested by bronchiolitis include, but not limited to, respiratory syncytial viruses (RSV), rhinoviruses, coronaviruses, enteroviruses, influenza A and/or B viruses, parainfluenza 1, 2 and/or 3 viruses, bocaviruses, human metapneumoviruses, SARS and adenoviruses. However, infections caused by any other viruses are also contemplated.

According to an aspect of some embodiments of the present invention, there is provided a method of treating a human subject suffering from a disease or a disorder which is associated, directly or indirectly, with a pathogenic microorganism, as to described herein. The method is effected by subjecting the subject to intermittent breathing cycle-coordinated pulse delivery inhalation regimen of gNO at a concentration of at least 160 ppm, or at a load per cycle of 80 ppm-hour, as described in any of the present embodiments.

According to another aspect of some embodiments of the present invention, there is provided a method of treating a human subject suffering from a disease or disorder that is manifested in the respiratory tract or a disease or disorder that can be treated via the respiratory tract, which is effected by subjecting the subject to intermittent breathing cycle-coordinated pulse delivery inhalation regimen, gNO at a concentration of at least 160 ppm, or at a load per cycle of 80 ppm-hour, as described in any of the present embodiments.

According to another aspect of some embodiments of the present invention, there is provided a method of treating a human subject prone to suffer from a disease or disorder that is manifested in the respiratory tract or a disease or disorder that can be treated via the respiratory tract, as described herein, which is effected by subjecting the subject to intermittent breathing cycle-coordinated pulse delivery inhalation regimen, gNO at a concentration of at least 160 ppm, or at a load per cycle of 80 ppm-hour, as described in any of the present embodiments. Such a method can be regarded as a preventive or prophylaxis treatment of the subject.

According to another aspect of some embodiments of the present invention, there is provided a method of treating a human subject suffering from an ophthalmological, otolaryngological and/or upper respiratory tract disease or disorder, as described herein, which is effected by subjecting the subject to intermittent breathing cycle-coordinated pulse delivery inhalation regimen, gNO at a concentration of at least 160 ppm, or at a load per cycle of 80 ppm-hour, as described in any of the present embodiments.

According to some embodiments of the present invention, the otolaryngological and/or upper respiratory tract disease and disorder involves an infection or an inflammation of a bodily site selected from the group consisting of an ear cavity, a nasal cavity, a sinus cavity, an oral cavity, a pharynx, a epiglottis, a vocal cord, a trachea, an apex and an upper esophagus.

According to some embodiments of the present invention, the ophthalmological, otolaryngological and/or upper respiratory tract diseases and to disorders include, without limitation, the common cold, a stomatognathic disease, amigdalitis, an oral fungal infection, bacterial-, viral- and/or fungal sinusitis, bronchitis, candidiasis of the oral cavity (thrush), canker sores, epiglottitis (supraglottitis), halitosis, herpes, laryngitis, laryngotracheitis, nasopharyngitis, otitis (externa and media), conjunctivitis, uveitis and other eye infections, pharyngitis, rhinitis, rhinopharyingitis, rhinosinusitis, stomatitis, tonsillitis, tracheitis, tracheitis and tympanitis.

According to another aspect of some embodiments of the present invention, there is provided a method of treating a human subject suffering from a disease or disorder of the lower respiratory system, as described herein, by intermittent breathing cycle-coordinated pulse delivery inhalation regimen, gNO at a concentration of at least 160 ppm, or at a load per cycle of 80 ppm-hour, as described in any of the embodiments herein.

According to some embodiments of the present invention, diseases and disorders of the lower respiratory system include, without limitation, an obstructive condition, a restrictive condition, a vascular disease and an infection, an inflammation due to inhalation of foreign matter and an inhaled particle poisoning.

According to some embodiments of the present invention, the obstructive condition includes, without limitation, a chronic obstructive lung disease (COPD), emphysema, bronchiolitis, bronchitis, asthma and viral, bacterial and fungal exacerbated asthma; the restrictive condition includes, without limitation, fibrosis, cystic fibrosis, sarcoidosis, alveolar damage and pleural effusion; the vascular disease includes, without limitation, pulmonary edema, pulmonary embolism and pulmonary hypertension; the infection includes, without limitation, respiratory syncytial virus infection, tuberculosis, a viral-, bacterial-, fungal-, and/or parasitic pneumonia, idiopathic pneumonia; and the inflammation due to inhalation of foreign matter and an inhaled particle poisoning includes, without limitation, smoke inhalation, asbestosis and exposure to particulate pollutants and fumes.

According to some embodiments of the present invention, any of the methods of treating or preventing a subject as described herein encompasses all of the conditions, disease and disorders described hereinabove for subjects in need of gNO inhalation.

It is noted herein that any of the methods described herein can be used to beneficially to treat bronchiolitis, which occurs in infants and children. Administration by inhalation is considered to be a preferred method of for young patients and more so when invasive techniques are avoided.

Influenza of all sorts and types is also treatable by the methods presented herein, and where some embodiments being based on a relatively simple and noninvasive techniques, these methods are particularly preferred in complicated and severe cases of influenza.

The methods presented herein are effective in treating asthma in children and adults, as well as treating COPD and CF.

The methods presented herein are fast and effective in treating a resent medical condition, disease or disorder. Moreover, the methods presented herein are effective in preventing the disease or disorder from taking hold in a subject which is prone to suffer from, contract or develop a disease or disorder which is associated with the respiratory tract. According to some embodiments, some methods of gNO inhalation are particularly useful in preventing a disease or disorder, while other methods are particularly effective in treating an existing disease or disorder.

According to some embodiments of the present invention, the method is used to treat a human subject suffering from a disease or disorder that is manifested in the respiratory tract or a disease or disorder that can be treated via the respiratory tract, which is associated with a nosocomial infection, wherein the method is effected by subjecting the subject to intermittent breathing cycle-coordinated pulse delivery inhalation of gNO at a concentration of at least 160 ppm, or at a load per cycle of 80 ppm-hour, essentially as described in any one of the embodiments herein.

According to some embodiments of the present invention, any of the methods described herein can be used in the context of the following conditions:

Any of the methods presented herein can be used effectively to treat respiratory diseases or disorders that occur in humans which are diagnosed with medical conditions that adversely affect their innate immune system. Humans which are diagnosed with such medical conditions are said to be immuno-compromised or immuno-suppressed. It is noted herein that immuno-suppression may be a direct result of a pathogen, such as an HIV infection, or an indirect result such as immuno-suppression that occurs in cancer patients being treated with chemotherapeutic to agents. Hence, according to some embodiments of the present invention, the methods presented herein are used to treat a present respiratory disease or disorder in immuno-compromised human subject.

According to some embodiments of the present invention, subjecting the subject to intermittent breathing cycle-coordinated pulse delivery inhalation of gNO at a concentration of at least 160 ppm, or at a load per cycle of 80 ppm-hour, as described in any one of the embodiments herein, is used in a method of treating a human subject suffering from, prone to suffer from or being at risk of suffering from, a disease or disorder that is manifested in the respiratory tract or a disease or disorder that can be treated via the respiratory tract, which is associated with an opportunistic infection, e.g., in an immune-compromised subject.

According to some embodiments, a method of subjecting a human subject to intermittent breathing cycle-coordinated pulse delivery inhalation of gNO inhalation as described in any one of the embodiments herein, is highly effective for treating respiratory diseases or disorders in subjects which are diagnosed with medical conditions that adversely affect their innate immune system. Humans which are diagnosed with such medical conditions are said to be immuno-compromised or immuno-suppressed.

According to some embodiments of the present invention, the method is used for treating a human subject prone to suffer from, or being at risk of suffering from, a disease or disorder that is manifested in the respiratory tract or a disease or disorder that can be treated via the respiratory tract, wherein the disease or disorder is associated with an opportunistic infection in an immuno-compromised subject.

By "prone to suffer" in the context of opportunistic infections it is meant that the human subject is at a higher risk of suffering from the indicated disease or disorder compared to a normal subject, such as, but not limited to, immune-compromised subjects as described herein.

According to embodiments of the present invention, any of the methods of treating an opportunistic infection in an immuno-compromised subject is effected by subjecting the subject to intermittent breathing cycle-coordinated pulse delivery inhalation of gNO at a concentration of at least 160 ppm, or at a load per cycle of 80 ppm-hour, as described herein.

It is noted herein that immuno-suppression may be a direct result of a pathogen, such as an HIV infection, or an indirect result such as immuno-suppression that occurs in cancer patients being treated with chemotherapeutic agents. Hence, according to some embodiments of the present invention, the methods presented herein are used to treat or prevent a respiratory disease or disorder in immuno-compromised human subject.

Immuno-compromised or immuno-suppressed human subjects are intrinsically more susceptible to opportunistic infections, rendering them prone to suffer from respiratory diseases or disorders Immuno-suppression may be a result of several conditions, including without limitation, pregnancy, malnutrition, fatigue, recurrent infections, administration of immuno-suppressing agents (such as for organ transplant recipients), advanced HIV infection, chemotherapy (such as for cancer treatment), a genetic predisposition, skin damage, antibiotic treatment, and several other medical procedures.

In some exemplary embodiments, such human subjects include, but are not limited to, immuno-compromised subjects such as subjects having HIV, cancer patients undergoing or which underwent chemotherapy, and cancer and other patients undergoing or which underwent transplantation, including bone marrow transplantation and transplantation of a solid organ, which are prone to or are at risk to suffer from a respiratory disease or disorder associated with an opportunistic infection.

Alternatively, a human subject in need of gNO treatment is an immuno-compromised subject such as subjects having HIV, cancer patients undergoing or which underwent chemotherapy, cancer and other patients undergoing or which underwent transplantation, including bone marrow transplantation and transplantation of a solid organ, which have been infected or otherwise suffer from a respiratory disease or disorder associated with opportunistic infection.

In the context of embodiments of the present invention, the term "immuno-suppression" is used interchangeably with the term "immunodeficiency" or "immune deficiency", which is a more general primary or secondary state in which the immune system's ability to fight infectious disease is compromised or entirely absent. While most cases of immunodeficiency are acquired ("secondary"), some subjects are born with defects in their immune system, which is then referred to as primary immunodeficiency.

As used herein, the term "opportunistic infection" refers to bacterial, viral, fungal or protozoan infection caused by opportunistic pathogens that may or may not cause diseases in healthy hosts having a functioning immune system. These pathogens may cause an opportunistic infection since a compromised immune system presents an "opportunity" for such pathogens to thrive in an immuno-compromised subject.

Exemplary opportunistic infections, which occur in human suffering from HIV, and can be treated or prevented by the methods presented herein include, without limitation *pneumocystis jiroveci* infection, *pneumocystis carinii* infection and *pneumocystis* pneumonia (a form of pneumonia caused by the yeast-like fungus).

Other non-limiting examples of opportunistic infection-causing pathogens include *Acinetobacter baumanni, Aspergillus sp., Candida albicans, Clostridium difficile, Cryptococcus neoformans, Cryptosporidium, Cytomegalovirus, Geomyces destructans, Histoplasma capsulatum, Isospora belli*, Polyomavirus JC polyomavirus (virus that causes Progressive multifocal leukoencephalopathy, Kaposi's Sarcoma caused by Human herpesvirus 8 (HHV8, also called Kaposi's sarcoma-associated herpesvirus KSHV), Legionnaires' Disease (*Legionella pneumophila*), Microsporidium, *Mycobacterium avium* complex (MAC) (*Nontuberculosis Mycobacterium*), *Pneumocystis jirovecii* (previously known as *Pneumocystis carinii* f. *hominis*), *Pseudomonas aeruginosa, Staphylococcus aureus, Streptococcus pneumoniae, Streptococcus pyogenes* and *Toxoplasma gondii*.

Exemplary medical conditions which are associated with immunosuppression include AIDS, cancer, primary ciliary dyskinesia (PCD, also known as immotile ciliary syndrome or Kartagener Syndrome).

According to some embodiments of the present invention, any of the methods presented herein is used to treat a human subject suffering from AIDS.

According to some embodiments of the present invention, any of the methods presented herein are used to treat a human subject suffering from cancer.

According to some embodiments of the present invention, any of the methods presented herein can be used to treat or prevent an infection associated with immune deficiency. These include prevention/pre-emptive treatment and treatment of infections in oncology patients.

According to some embodiments of the present invention, any of the methods to described herein can be used effectively to treat any respiratory diseases or disorders that occur in humans, as described herein.

According to some embodiments of the present invention, in any of the methods presented herein the human subject is at risk of suffering from a nosocomial infection.

According to some embodiments of the present invention, subjecting the subject to intermittent breathing cycle-coordinated pulse delivery inhalation of gNO at a concentration of at least 160 ppm, or at a load per cycle of 80 ppm-hour, as described in any one of the embodiments herein, is used in a method of treating a human subject suffering from, prone to suffer from or being at risk of suffering from, a disease or disorder that is manifested in the respiratory tract or a disease or disorder that can be treated via the respiratory tract, which is associated with a nosocomial infection.

In the context of embodiments of the present invention "hospital-acquired infection", also known as a HAI or in medical literature as a "nosocomial infection", is an infection whose development is more prevalent in a hospital environment, such as one acquired by a patient during a hospitalization or a visit, or one developing among hospital staff. Such infections include fungal and bacterial infections and are aggravated by the reduced resistance of individual patients and the heightened resistance of the pathogens. In the context of the present invention, the term "nosocomial infection" is meant to encompass infections which are more prevalent also in environments other than hospitals and clinics, and include residence facilities for elderly people, veterinary facilities, farms and any livestock-handling facilities, kindergartens and schools, airplanes, boats trains and other mass transportation means and facilities, and any other environment where humans and/or livestock congregate.

By "prone to suffer" in the context of nosocomial infections it is meant that the human subject is at a higher risk of suffering from the indicated disease or disorder compared to a normal subject, such as, but not limited to subjects that spend over than average time (10% and more time than the average ordinary person) in environments wherein nosocomial infections are more prevalent.

According to some embodiments of the present invention, human subjects which are generally more exposed to nosocomial infections and are therefore more to prone to suffer from diseases or disorders due to general, environmental and occupational conditions include, without limitation, hospital/clinic patients, elderly people, medical staff and personnel (doctors, nurses, caretakers and the likes) of medical facilities and other care-giving homes and long-term facilities, teachers, train conductors, commercial boat and airline crew and personnel (pilots, flight attendants and the likes), livestock farmers and the likes.

Other incidents and conditions that render a human more susceptible to infections are associated with location, occupation, age, living and environmental conditions, close contact with large groups of people and livestock, close contact with sick people and the likes, all of which are encompassed in the context of the present invention as rendering a human subject prone to suffer from a respiratory disease or disorder associated with nosocomial infection.

According to some embodiments of the present invention, a human subject is in need of preemptive, preventative and prophylactic treatment of a primary and/or secondary disease or disorder as described hereinbelow. Hence, a subject not suffering from any current or manifested disease, and/or a subject that is suspected of being exposed to a pathogen, and/or a subject that suffers from one disease, is treated by any of the methods presented herein in order to prevent the occurrence of another disease or disorder (secondary disease or disorder).

According to some embodiments, the methods presented herein are used to treat or prevent nosocomial infections, such as infections stemming from direct-contact transmission, indirect-contact transmission, droplet transmission, airborne transmission, common vehicle transmission and vector borne transmission.

The methods presented herein are effective to treat diseases and disorders which are caused by any pathogen, as described hereinbelow, including without limitation, pathogens which are known to cause nosocomial infections.

Non-limiting examples of nosocomial infection-causing pathogens include antibiotic resistant bacteria such as carbapenem-resistant *Klebsiella* (KPC) or other Enterobacteriaceae, Group A *Streptococcus* species, methicillin resistance *Staphylococcus Aureus* (MRSA), methicillin sensitive *Staphylococcus aureus*, *E. coli* O157:H7, vancomycin-resistant *Enterococcus* species (VRE), *Enterobacter aerogenes*, *Clostridium difficile*, *Acinetobacter* species such as *A. baumannii*, *Klebsiella pneumonia*, *Pseudomonas aeruginosa*, *Neisseria meningitides* of any serotype and the likes.

Hence, according to embodiments of the present invention, the methods presented herein can be used to prevent carriage, transmission and infection of pathogenic bacteria and antibiotic resistant pathogenic microorganisms.

According to some embodiments of the present invention, any of the methods of treatment presented herein further includes monitoring, during and following administration gNO, one or more of the parameters as described in any of the embodiments hereinabove.

In some embodiments, the methods are effected while monitoring one, two, etc., or all of:

a methemoglobin level (SpMet) (an on-line parameter);
an end-tidal $CO_2$ level ($ETCO_2$) (an on-line parameter);
an oxygenation level or oxygen saturation level ($SpO_2$) (an on-line parameter);
an inflammatory cytokine plasma level (an off-line parameter); and
a serum nitrite/nitrate level ($NO_2^-/NO_3^-$) (an off-line parameter).

In some embodiments, no significant deviation from baseline, as described herein, is shown in at least one, two, three, four or all of the above parameters, when monitored, as described herein.

Other parameters and markers may be monitored as well, as presented hereinabove, while showing significant deviation from a baseline, and various general health indicators show no change to the worse, or an improvement, as presented hereinabove.

According to some embodiments of the present invention, in any of the methods of treatment presented herein, the gNO administration can be effected by an inhalation device which includes, without limitation, a breathing cycle-coordinated pulse delivery inhalation device, a stationary inhalation device, a portable inhaler, a metered-dose inhaler and an intubated inhaler.

Referring now to the drawings, FIG. 3 presents a schematic illustration of an exemplary breathing cycle-coordinated pulse delivery inhalation device 20, suitable for executing the methods according to some embodiments of the present invention. Gas cylinder 11 is the source of nitric oxide. Preferably NO gas is mixed with a to balance or carrier gas such as nitrogen and the concentration may be in the range of 80 ppm to 900 ppm, or 160 ppm to 800 ppm. The NO in nitrogen gas is available commercially in cylinders at pressures from about 2000 psig to about 2400 psig.

Pressure regulator 12 reduces the cylinder pressure to a pressure suitable for use with the present method and that pressure may be in the order of about 50 psig. Pressure gauge 14 is generally provided on pressure regulator 12 in order to keep track of the pressure within gas cylinder 11.

Conduit 16 carries the NO containing inhalant from pressure regulator 12 through to patient 18 where the NO containing inhalant is administered to patient 18 by means such as a facial respiratory mask or a nasal respiratory mask (not shown). Branching from conduit 16 is purge line 20 and purge valve 22. As can be seen, purge valve 22 is normally in the non-energized position blocking the flow of gas therethrough and is activated by central processing unit (CPU) 24 to open purge valve 22 to clear of gas certain portions of conduit 16 as well as pressure regulator 12. Thus, when gas cylinder 11 is opened, on initial use of the equipment, the NO containing inhalant flows through pressure regulator 12, a portion of conduit 16 and, purge line 20 and is exhausted out purge valve 22 to rid those passages of air and thus to make sure that the oxygen present in air cannot act on the NO to create $NO_2$.

Operation of purge valve 22 may be immediate by CPU 24 upon start up of the apparatus or may be accomplished manually with a prompt from a display operated by CPU 24.

Control valve 26 controls the flow of NO containing inhalant from gas cylinder 11 to patient 18 and is a solenoid controlled valve operated by signal from CPU 24. For safety, control valve 26 is normally closed and is moved to its open position when a signal energizes the valve by CPU 24. As will be explained, the time during which the control valve is in the open position controls the volume of NO containing inhalant delivered to patient 18.

Fixed restrictor 28 is also provided in conduit 16 and may be a commercially available restrictor and which is provided with the pressure to flow characteristics by the supplier. Upstream of fixed restrictor 28 is absolute pressure transducer 30 which senses the absolute pressure in conduit 16 as $P_{control}$. That pressure is also communicated to CPU 24. Absolute pressure transducer 30 is of the type that operates off a base of zero psi and therefore it reads the absolute pressure within to conduit 16 at the point just upstream of fixed restrictor 28. By the absolute pressure, the reading takes into account also the ambient pressure surrounding the apparatus. Typical pressure transducers of the absolute pressure type are available, for example, from Sensyn, Inc.

Accordingly, CPU 24 is in receipt of the information necessary to determine the exact flow of NO containing inhalant through fixed restrictor 28 and thus, the flow to patient 18. The characteristics of any particular fixed restrictor are available from the manufacturer as a curve or other data that can be used by CPU 24 as a look up table or the like. Since the flow through fixed restrictor 28 is directly proportional to the absolute pressure of the gas entering fixed restrictor 28, CPU 24 is also in possession the $P_{control}$ from absolute pressure transducer 30 and thus can readily calculate the flow to patient 18.

Patient trigger 32 is in communication with patient 18 by means of passageway 34 and may include check valve 36. Patient trigger 32 may be of conventional design and basically detects a negative pressure $P_{trigger}$ from the patient indicating that patient 18 is initiating inhalation. Patient trigger 32 thus provides a signal to CPU 24 to alert CPU 24 that the patient is initiating an inhalation so that CPU 24 can effect the appropriate action to provide a pulse of NO containing inhalant to patient 18 during that inhalation.

Operator input device 38 allows the operator to input to CPU 24 the specific volume of NO containing inhalant that is desired to be delivered to patient 18 during each inhalation and such device may be a rotary switch or the like. Alternatively, the volume to be delivered may be predetermined by the manufacturer of the delivery system and already established in the system and not be individually selected in the field by an operator. Also as a part of the system, there may be audio alarm 40 and visual display 42 that may also contain visual alarms as well as display various monitored conditions of the device to the operator.

The overall operation of breathing cycle-coordinated pulse delivery inhalation device 20 refers to embodiments where the operator of the device makes the desired selection of the volume to be administered to the patient. As noted, upon start-up of the system, gas cylinder 11 containing the NO inhalant in a predetermined concentration is opened and the NO containing inhalant enters pressure regulator 12 and conduit 16. Purge valve 22 is opened by a signal from CPU 24 or manually by a to prompt displayed on visual display 42 so that pressure regulator 12 and the portion of conduit 16 are purged off.

The operator inputs a volume of NO containing inhalant that is desired to be administered to patient 18 by means of operator input device 38. As patient 18 initiates an inhalation, patient trigger 32 senses the negative pressure and signals CPU 24 to commence the injection of a dosage of NO containing inhalant to patient 18. Initially, CPU 24 opens control valve 26 for a predetermined time (pulse-on 130 in FIG. 2) based upon a calibration curve that is determined at the factory at known ambient pressure and temperature and is incorporated into the device. The ambient pressure is sensed at the location of the use of the NO administration device and a correction made by CPU 24 to arrive at a period of time that control valve 26 is opened by CPU 24 to allow a volume of gas to pass therethrough to patient 18 and then will move control valve 26 to its closed position.

CPU 24 can now calculate the exact volume of gas delivered to patient 18, using the data that is representative of the characteristics of fixed restrictor 28 and the input it receives from absolute pressure transducer 30 of $P_{control}$. With that data and the amount of time that control valve 26 has been opened, CPU 24 can readily calculate the exact volume by integrating the flow through fixed restrictor 28 with respect to the time control valve 26 is in its open position and arrive at the volume of NO containing inhalant administered to patient 18.

With the calculated volume, CPU 24 can then compare the volume calculated with the volume that has been inputted by the operator as the desired volume for administration to patient 18. CPU 24 can thus alter the time control valve 26 is opened and recalculate until the volume that it calculates is the same as the volume inputted by the operator in operator input device 38. At this point, the overall device can administer an operator set precise volume of NO containing inhalant at each inhalation triggered by patient 18.

As other safety measures of breathing cycle-coordinated pulse delivery inhalation device 20, it is possible to detect the failure of control valve 26 based on data from the $P_{control}$ and the known timing of the control valve sequence. For example, if there is no rise in the value of $P_{control}$ by a known amount, based upon a minimum supply pressure, and control valve 26 has been given a signal to open by CPU 24, then the system will recognize a failure to deliver the therapy to patient 18 to and a suitable alarm may be activated at audio alarm 40 and/or by a visual alarm indication on visual display 42. Conversely, if the $P_{control}$ is not reduced by a known amount, based upon the minimum supply pressure, and control valve 26 has been given the signal to close by CPU 24, then the system can detect a delivery error and again an audible or visual alarm is activated. Thus one can establish safe limits for delivery of NO and therefore a fault condition can be detected based on the established safe limits.

Similarly, breathing cycle-coordinated pulse delivery inhalation device 20 can activate audio alarm 40 and/or the indicate an alarm condition on visual display 42 by sensing the volume of gas that passes through conduit 16, that is, if the signal is provided to close control valve 26 and the determination of volume of gas passing through conduit 16 does not cease, it is an indication of a fault and an appropriate response is initiated. In the same manner, breathing cycle-coordinated pulse delivery inhalation device 20 can determine the flow in conduit 16 to check that the flow ceases or starts based on the triggered position of control valve 26 to, again, determine a fault condition and provide an alarm to alert the operator of that condition.

Turning now to FIG. 4, there is shown a schematic illustration of an embodiment of breathing cycle-coordinated pulse delivery inhalation device 20 where the ambient temperature is taken into account in determining the correct time to open the control valve to obtain a precise dose of inhalant to be administered to the patient.

In the embodiment presented in FIG. 4, some of the components are the same as used in the embodiment presented in FIG. 3, hence those components have utilized the same reference numerals. In this embodiment, however, there is the addition of temperature sensor 44 that senses the temperature $T_0$ of the NO containing inhalant prior to its passing through fixed restrictor 28. In addition, an ambient pressure sensor and temperature sensor have been added and those sensors are both depicted by block 46. The dose can be corrected to a fixed temperature and pressure (and hence be a mass dose) or corrected to the ambient temperature and pressure (and hence be a volumetric dose).

In the operation of the embodiment presented in FIG. 4, it is noted that the system takes into account the temperature and pressure of the gas passing through fixed restrictor 28 as well as the ambient pressure and temperature in order to determine the dosage of NO containing inhalant to the patient. Again, gas cylinder 11 is opened and the NO containing inhalant enters pressure regulator 12 and conduit 16. A purge valve is not shown in FIG. 4, however, one can be used in the overall system similar to the embodiment presented in FIG. 3.

The operator inputs the desired volumetric dosage to be delivered to the patient with operator input device 38. Patient trigger 32, again, senses the negative pressure representative of the patient attempting to inhale and patient trigger 32 signals CPU 24 to commence the introduction of the NO containing inhalant to patient 18. Initially, CPU 24 opens control valve 26 for a period of time calculated by CPU 24 based on the dose inputted by the operator, $V_{set}$. That open time, $T_{INITIAL}$, is based on the curve that was established founded upon the calibration conditions at the factory in initially setting up the system. The system, as manufactured, is calibrated to determine the volumes delivered for times control valve 26 is open and is operated at the conditions in the manufacturing facilities during calibration, which is $T_{CAL}$ and $P_{CAL}$ and a set of curves generated for the system.

In use, as the patient attempts to inhale, CPU 24 has information from block 46 with respect to the ambient pressure PA and the ambient temperature TA and can calculate the $V_{CAL}$ that needs to be provided to the patient for the dose inputted by the operator, Vset, based on the actual ambient conditions existing at the patient. Thus, by use of these parameters, CPU 24 can determine the $V_{CAL}$ and adjust to the ambient conditions to determine the time that control valve 26 need be opened to deliver the $V_{SET}$ to the patient at those ambient conditions.

The actually delivered dose can be determined as a check against the $V_{SET}$ by the measurements of the temperature and absolute pressure of the gas passing through fixed restrictor 28, the ambient temperature and pressure, as well as the known pressure flow characteristics of the restrictor or orifice.

Thus, by use of the volume of the pulse where the flow through the orifice was sonic ($V_{DEL}$), the constant for the orifice geometry and gas characteristics, the orifice gas pressure, the orifice gas temperature, the ambient pressure and the ambient temperature, the actual delivered flow can be determined and integrated with the time the control valve is in the open position to derive the $V_{DEL}$ to the patient. The volume delivered can then be compared with the volume established by the operator $V_{SET}$ and any error between the values can be used to modify the $T_{INITIAL}$ to become $T_{CONTROL}$ that will correct for any differences.

In another embodiment of the present invention, an alarm strategy is used to insure that the delivery device is properly delivering the dose that is desired. In the implementation of the alarm system, that dose actually delivered by the system, $V_{DEL}$, is compared with the $V_{SET}$ can be used to trigger an alarm if the values are different by a predetermined percentage. That is, if the actual delivered volume is more than a certain percentage, for example, thirty percent (30%), CPU 24 can recognize that the difference is indicative of a problem in the overall pulse delivery system and trigger audible alarm 40 and/or provide some visual alarm on the visual display 42.

Exemplary inhalation devices which may be suitable for the execution of any of the methods described herein, according to some embodiments of the present invention, are provided in, for example, U.S. Pat. Nos. 6,164,276 and 6,109,260, the contents of which are hereby incorporated by reference. Commercial inhalation devices which may be suitable for the execution of any of the methods described herein, include the INOpulse® DS-C developed by Ikaria Australia Pty Ltd, or the Ohmeda INOpulse Delivery System by Datex-Ohmeda.

An inhaler, according to some embodiments of the present invention, can generate spirometry data and adjust the treatment accordingly over time as provided, for example, in U.S. Pat. No. 5,724,986 and WO 2005/046426, the contents of which are hereby incorporated by reference. The inhaler can modulate the subject's inhalation waveform to target specific lung sites. According to some embodiments of the present invention, a portable inhaler can deliver both rescue and maintenance doses of gNO at subject's selection or automatically according to a specified regimen.

According to some embodiments of the present invention, an exemplary breathing cycle-coordinated pulse delivery inhalation device may include a delivery interface adaptable for inhalation by a human subject.

According to some embodiments of the present invention, the delivery interface includes a mask or a mouthpiece for delivery of the mixture of gases containing gNO to a respiratory organ of the subject.

According to some embodiments of the present invention, the breathing cycle-coordinated pulse delivery inhalation device further includes a gNO analyzer positioned in proximity to the delivery interface for measuring the concentration of to gNO, oxygen and nitrogen dioxide flowing to the delivery interface, wherein the analyzer is in communication with the controller.

According to some embodiments of the present invention, subjecting the subject to the method described herein is carried out by use of an inhalation device which can be any device which can deliver the mixture of gases containing gNO by breathing cycle-coordinated pulse delivery to a respiratory organ of the subject. An inhalation device, according to some embodiments of the present invention, includes, without limitation, a stationary inhalation device comprising tanks, gauges, tubing, a mask, controllers, values and the likes; a portable inhaler (inclusive of the aforementioned components), a metered-dose inhaler, a respiration machine/system and an intubated inhalation/respiration machine/system.

It is expected that during the life of a patent maturing from this application many relevant medical procedures involving inhalation of gNO will be developed and the scope of the term treatment by inhalation of gNO is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition, and substantially preventing the appearance of clinical or aesthetical symptoms of a condition, namely preemptive, preventative and prophylactic treatment.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad to scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a human subject in need of inhalation of gaseous NO (gNO), the method comprising subjecting the human subject to at least one cycle of intermittent inhalation of an inhalant, wherein the intermittent inhalation comprises inhalation of the inhalant for a first time period wherein the inhalant comprises gNO; followed by inhalation of essentially no gNO for a second time period;
   wherein the first time period of intermittent inhalation comprises at least one cycle of a breathing cycle-coordinated pulse delivery inhalation of said inhalant, wherein:
   said breathing cycle-coordinated pulse delivery inhalation comprises a pulse delay period, a pulse delivery period and a pulse cessation period;
   wherein said pulse delivery period comprises at least two pulse-on periods followed by a pulse-off period; and
   wherein said inhalant comprises no gNO during said pulse delay period, said pulse cessation period and an exhalation period of said breathing cycle-coordinated pulse delivery inhalation.

2. The method of claim 1, wherein said pulse delay period is greater than 0 ms and less than 2500 ms.

3. The method of claim 1, wherein said pulse cessation period is greater than 0 ms and less than 2500 ms.

4. The method of claim 1, wherein each of said pulse-on period individually ranges from 100 ms to 5000 ms.

5. The method of claim 4, wherein each of said pulse-off period individually is greater than 0 ms and less than 2500 ms.

6. The method of claim 1, wherein said pulse-on period is 260 ms.

7. The method of claim 1, wherein said first time period is about 30 minutes.

8. The method of claim 1, wherein said second time period ranges from 3 to 5 hours.

9. The method of claim 1, wherein said intermittent inhalation comprises from 1 to 6 of said cycles per day.

10. The method of claim 9, wherein said intermittent inhalation comprises 5 of said cycles per day.

11. The method of claim 1, wherein said intermittent inhalation is effected during a time period that ranges from 1 to 7 days.

12. The method of claim 1, wherein during said first time period, a concentration of $NO_2$ in said inhalant is less than 5 ppm.

13. The method of claim 1, wherein during said first time period, a concentration of $O_2$ in said inhalant ranges from 20% to 25%.

14. The method of claim 1, wherein during said first time period, a fraction of inspired oxygen level ($FiO_2$) in said inhalant ranges from 21% to 100%.

15. The method of claim 1, further comprising monitoring at least one on-site parameter in the subject selected from the group consisting of:
    a methemoglobin level (SpMet);
    an oxygen saturation level ($SpO_2$); and
    an end tidal $CO_2$ level ($ETCO_2$),
    and/or at least one off-site parameter selected from the group consisting of: a serum nitrite/nitrate level ($NO_2^-/NO_3^{31}$); and
    an inflammatory cytokine plasma level.

16. The method of claim 15, wherein said cytokine 1 s selected from the group consisting of (TNF)a, (IL)-113, IL-6, IL-8, IL-10 and IL-12p70.

17. The method of claim 15, comprising monitoring at least two of said parameters.

18. The method of claim 15, comprising monitoring all of said parameters.

19. The method of claim 15, wherein a change in said at least one of said parameters following said subjecting is less than 2 acceptable deviation units from a baseline.

20. The method of claim 1, wherein said inhalant comprises gNO at a concentration of at least 160 ppm during said pulse delivery period.

21. The method of claim 1, wherein a cycle of intermittent inhalation delivers at least about 80 ppm·hrs gNO.

22. The method of claim 1, wherein the pulse delay period is greater than 0% but less than 80% of the inhalation period.

23. The method of claim 1, wherein the pulse delay period is set to 1% of the inhalation period.

24. The method of claim 1, wherein the pulse delay period is set to 5% of the inhalation period.

25. The method of claim 1, wherein the pulse delay period is set to 20% of the inhalation period.

26. The method of claim 1, wherein the pulse delivery period is greater than 10% but less than 100% of the inhalation period.

27. The method of claim 1, wherein the pulse delivery period is set to 98% of the inhalation period.

28. The method of claim 1, wherein the pulse delivery period is set to 90% of the inhalation period.

29. The method of claim 1, wherein the pulse delivery period is set to 60% of the inhalation period.

30. The method of claim 1, wherein the pulse cessation period is greater than 0% but less than 80% of the inhalation period.

31. The method of claim 1, wherein the pulse cessation period is set to 1% of the inhalation period.

32. The method of claim 1, wherein the pulse cessation period is set to 5% of the inhalation period.

33. The method of claim 1, wherein the pulse cessation period is set to 20% of the inhalation period.

* * * * *

UNITED STATES PATENT AND TRADEMARK OFFICE
CERTIFICATE OF CORRECTION

PATENT NO. : 10,039,781 B2
APPLICATION NO. : 15/079328
DATED : August 7, 2018
INVENTOR(S) : Yossef Av-Gay, David Greenberg and Einav Levi Page 1 of 1

It is certified that error appears in the above-identified patent and that said Letters Patent is hereby corrected as shown below:

In the Claims

Column 47, Claim 15, Line 16-17: after "level" please replace "($NO_2^{-/}$ $NO_3^{31}$)" with --($NO_2^-/NO_3^-$)--;

Column 47, Claim 16, Line 19: after "cytokine" please replace "1 s" with --is--; and Column 47, Claim 19, Line 26: after "in" please delete "said".

Signed and Sealed this
Twenty-third Day of October, 2018

Andrei Iancu
*Director of the United States Patent and Trademark Office*